US009610153B2

(12) United States Patent
Lipshitz et al.

(10) Patent No.: US 9,610,153 B2
(45) Date of Patent: Apr. 4, 2017

(54) INTRA-OCULAR IMPLANT

(76) Inventors: Isaac Lipshitz, Herzlia Pituach (IL);
Yariv Lipshitz, Ra'anana (IL)

( * ) Notice: Subject to any disclaimer, the term of this patent is extended or adjusted under 35 U.S.C. 154(b) by 364 days.

(21) Appl. No.: 12/295,339

(22) PCT Filed: Apr. 10, 2007

(86) PCT No.: PCT/IL2007/000444
§ 371 (c)(1),
(2), (4) Date: Sep. 30, 2008

(87) PCT Pub. No.: WO2007/113832
PCT Pub. Date: Oct. 11, 2007

(65) Prior Publication Data
US 2009/0048671 A1 Feb. 19, 2009

(51) Int. Cl.
*A61F 2/16* (2006.01)
*G02B 17/08* (2006.01)
*G02C 7/08* (2006.01)

(52) U.S. Cl.
CPC .......... *A61F 2/1613* (2013.01); *A61F 2/1648* (2013.01); *A61F 2/1654* (2013.01); *G02B 17/086* (2013.01); *G02B 17/0808* (2013.01); *G02C 7/088* (2013.01)

(58) Field of Classification Search
USPC .......... 623/6.32, 6.33, 1.11, 6.22–6.26, 6.56, 623/6.62
See application file for complete search history.

(56) References Cited

U.S. PATENT DOCUMENTS

| 4,601,545 | A | | 7/1986 | Kern | |
|---|---|---|---|---|---|
| 4,632,844 | A | * | 12/1986 | Yanagihara et al. | 427/488 |
| 4,759,761 | A | | 7/1988 | Portnoy | |
| 4,787,903 | A | | 11/1988 | Grendahl | |
| 5,548,352 | A | * | 8/1996 | Dewey | 351/159.02 |
| 5,844,225 | A | * | 12/1998 | Kimock et al. | 235/462.01 |

(Continued)

OTHER PUBLICATIONS

International Preliminary Report on Patentability published Mar. 17, 2009 for PCT/IL07/000444 filed Apr. 10, 2007.
(Continued)

*Primary Examiner* — Andrew Iwamaye
*Assistant Examiner* — Leslie Lopez
(74) *Attorney, Agent, or Firm* — Edward Langer, ADV & Patent Attorney

(57) ABSTRACT

An intra ocular implant consisting of optical elements, adapted to forming images on the retina, especially useful in treating presbyopic patients, patients with AMD, patients with other diseases of the retina, and patients in which future development of retinal disorders may occur. An intra ocular implant wherein at least one mirror is operationally connected to the action of the ciliary muscle or its effect on the zonules and capsule of the natural lens; and wherein the mirror is adapted to change curvature, position or optical properties, such that bringing a plurality of objects at different distances into focus is facilitated in presbyopic patients. A lens assembly comprising an intra ocular lens and, an adjustable external or contact lens comprising at least in part of light polarizing material; the assembly at least partially polarizes at least part of the central visual field, at least part of the peripheral visual field or both in any angle.

15 Claims, 23 Drawing Sheets

(56) References Cited

U.S. PATENT DOCUMENTS

Figure 1A:
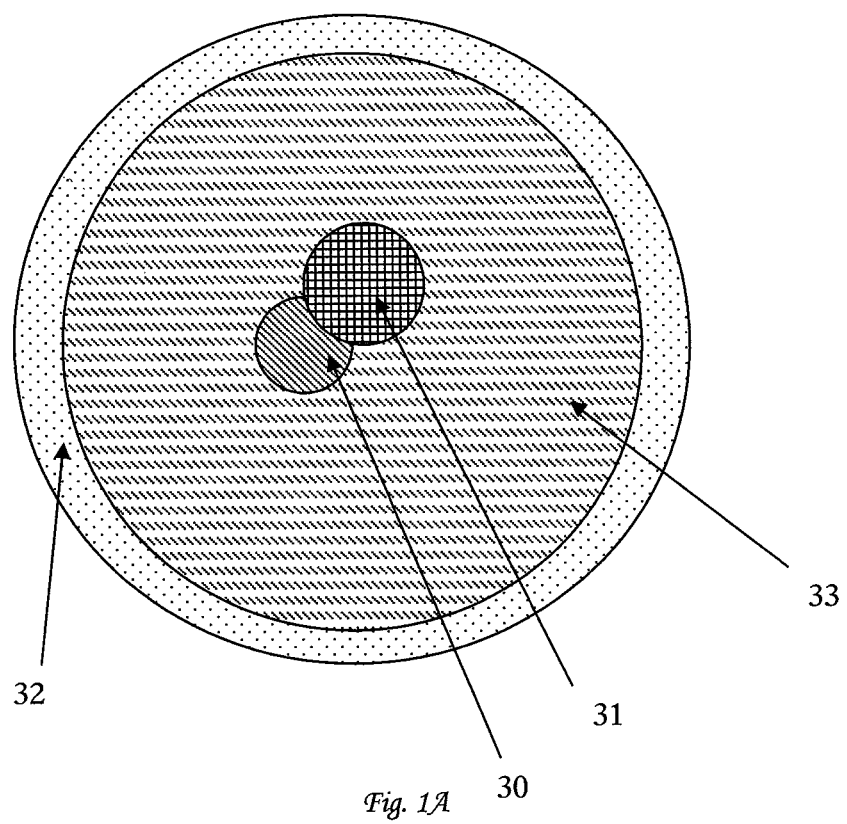

| | | | |
|---|---|---|---|
| 6,164,777 A * | 12/2000 | Li et al. | 351/159.02 |
| 6,794,066 B2 * | 9/2004 | Macchi et al. | 428/701 |
| 6,902,399 B2 | 6/2005 | Mannschedel | |
| 6,902,577 B2 | 6/2005 | Lipshitz et al. | |
| 6,920,399 B2 | 7/2005 | Priev et al. | |
| 7,008,448 B2 | 3/2006 | Lipshitz et al. | |
| 7,842,086 B2 * | 11/2010 | Dotan et al. | 623/6.17 |
| 2003/0187502 A1 * | 10/2003 | Lipshitz | 623/6.11 |

OTHER PUBLICATIONS

International Search Report mailed Mar. 26, 2008 for PCT/IL07/00444 filed Apr. 10, 2007.
Written Opinion of the International Searching Authority mailed Mar. 26, 2008 for PCT/IL07/00444 filed Apr. 10, 2007.

* cited by examiner

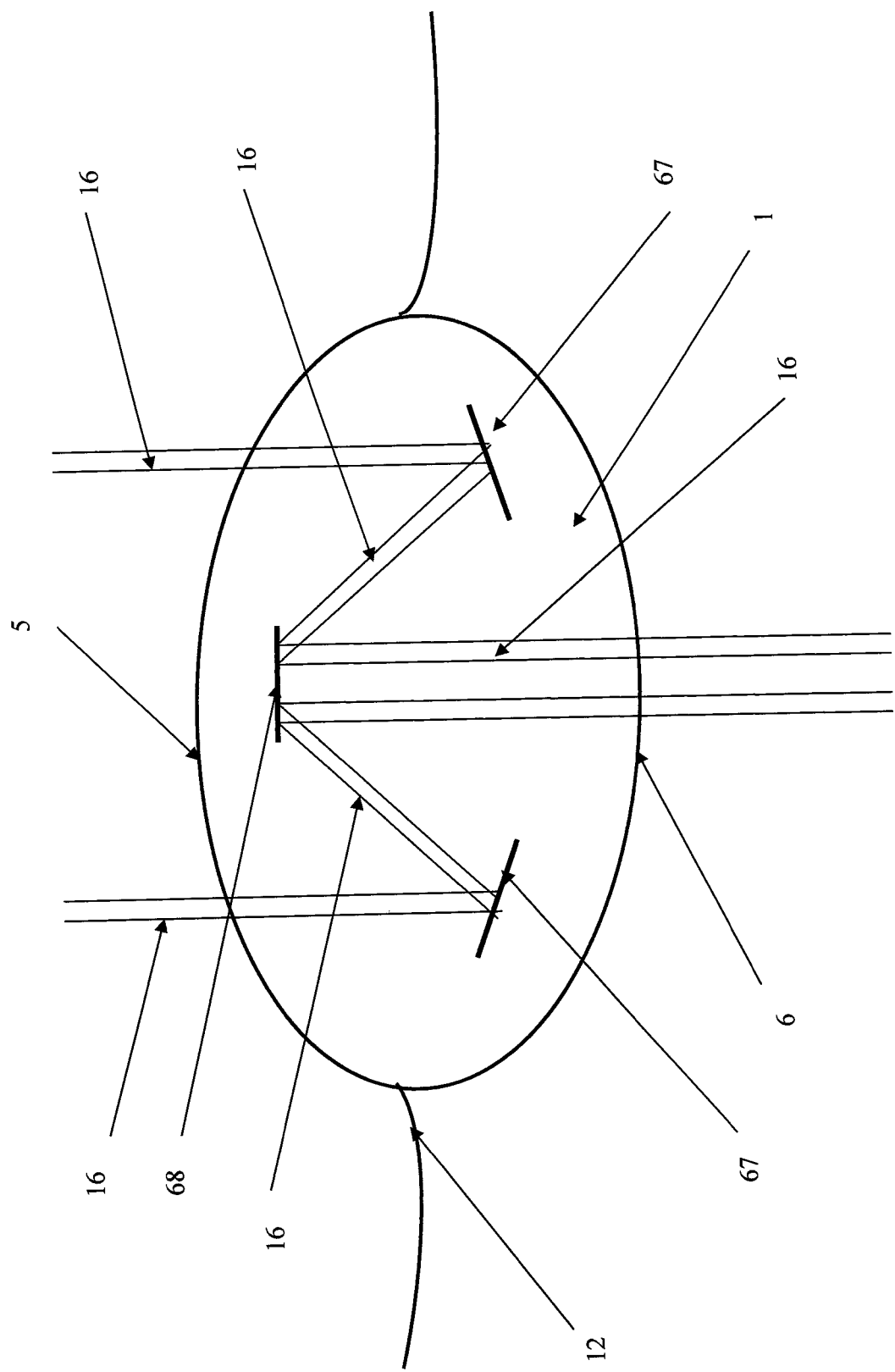

INTRA-OCULAR IMPLANT

CROSS-REFERENCE TO RELATED APPLICATIONS

This application is a national stage of PCT/IL07/00444, filed Apr. 10, 2007, which claims priority to Provisional Application No. 60/788,096 filed Apr. 3, 2006, and Provisional Application No. 60/845,942 filed Sep. 21, 2006.

FIELD OF THE INVENTION

This invention relates to an intra-ocular implant useful in improving vision in patients suffering from AMD and other retinal diseases and presbyopia.

BACKGROUND OF THE INVENTION

This new disclosure is an improvement over the teaching of U.S. Pat. No. 4,759,761 by Portnoy and U.S. Pat. Nos. 6,902,577, 6,920,399, 7,008,448 by Lipshitz et al. These patents disclose an intra-ocular implant that contains mirrors for modifying central vision for patients who suffer from retinal diseases such as macular degeneration (AMD) and for the treatment of presbyopia. The above-mentioned patents deal with changing (increasing or decreasing) the size of an object on the central retina as needed for AMD and other retinal patients. The above-mentioned patents suffer from several shortcomings.

U.S. Pat. No. 4,759,761 describes an implant creating one magnified image on the retina, but the implant as shown is smaller than the pupil opening, and this limits the visual improvement that can be achieved using the implant. The implant comprises of mirrors only. The mirrors are not combined with other optical tools and are designed to assist patients suffering from Age-related macular degeneration and not other retinal diseases. Furthermore, lens capsular bag or iris-supported implantations, which are known to be popular and effective, are not included in the above-mentioned patent. The mirrors in that patent are spherical, which prevents the user from getting the optical qualities that are required. The mirrors are embedded inside the implant making them much more complicated to manufacture than mirrors that are attached or vaporized on the surface of the implant. The invention taught in the patent does not answer the need of patients who have undergone cataract surgery and the implant is not designed as a secondary implant, added to an existing intra ocular lens in the eye.

U.S. Pat. Nos. 6,902,577, 6,920,399, 7,008,448 by Lipshitz et al. describe an implant with only one central visual field and one peripheral visual field but they do not address implants with more than one central field and/or more than one peripheral field. Under those patents, the central field may be magnified, whilst the peripheral field is left unchanged, but the magnification creates an under illuminated image on the center of the retina compared to the periphery and both images may overlap at least partially. There is a need to assist the patient in detecting both images and seeing the differences between the fields and in reducing the overlap and reducing the differences in illumination between those images so that the patient would be able to detect the central image as well.

Both Portnoy's patent (one magnified image) and Lipshitz's patents (an option of more than one image on the retina) mentioned above, describe an implant made of one piece. Depending on the configuration of the mirrors in those implants, it is difficult or impossible to manufacture such implants made of a single piece. An assembly of two or more pieces, manufactured separately is needed. Those implants cannot be manufactured with mirrors that are not dielectric or mirrors that not vaporized. Not all of the materials that make the mirrors and the implants' body member are sufficiently proven to be biocompatible and there is need to prevent the eye from coming into contact with hazardous and toxic materials. Furthermore, the patents above do not answer the need of patients undergoing cataract surgery for an implant with a solution to a progressive disease that during the cataract implantation is either still non-existent or gradually becoming more severe.

Prior art on intra ocular implants intended to help individuals suffering from presbyopia (need for reading glasses) discloses implants with lenses, diffractive optics elements and prisms but does not include implants with mirrors, whether combined or not with other optical components. Lipshitz (U.S. Pat. No. 6,920,399) discloses an implant with dynamic mirrors that are regulated from the outside of the eye but are not affected from within the eye by the ciliary muscle or its effect. There is a need for a dynamic intra ocular implant with optical components such as mirrors that are small enough and can change their properties and position in order to support psuedo-accommodation.

Existing static designs of intra ocular implants that create more than one focal point for patients suffering from presbyopia do not include mirrors.

For patients with various retinal and non-retinal eye diseases, there is a need for an intra ocular implant that helps the patient determine the light illumination that he needs in any part of his retina, also enabling the patient to control relative light illumination between different parts on the retina.

SUMMARY OF THE INVENTION

It is in the scope of the invention wherein an intra ocular implant is disclosed. The implant comprises (a) a body member having optical properties; and, (b) an optical arrangement adapted to form at least one first image and at least one second image on the retina. The arrangement comprises of the body member and at least one means selected from a group consisting inter alia of diffractive optics elements, adaptive optics elements, Fresnel prisms, lenses, mirrors, prisms, liquid crystal elements or any combination thereof. The aforesaid at least one first image comprises of at least part of the peripheral visual field. The aforesaid at least one second image comprises of at least part of the central visual field.

It is in the scope of the invention wherein the implant further comprises of one or more means to provide perceivable differences between the first and the second images on the retina, hence enabling the patient to differentiate between the visual fields. The perceivable differences are based on one or more criteria selected in a non-limiting manner from a group consisting of differences in contrast; location; transmitted light spectra; color; magnification; illumination or focus.

It is also in the scope of the invention wherein the implant as defined in any of the above further comprises of means of decreasing the overlap and/or the differences in illumination between the first and the second images on the retina.

It is also in the scope of the invention wherein secondary intraocular implant is disclosed. This implant is especially adapted for implantation into a psuedophakic eye. It may comprise of at least one loop for fixating the implant in the eye, in such a way that at least part of the loop is placed inside the capsular bag and at least part of said implant's body member is placed outside said capsular bag.

It is also in the scope of the invention wherein an implant as defined in any of the above comprises of at least one first piece and at least one second piece. The first piece comprises of at least one optical element, selected inter alia from a group consisting of diffractive optics elements, adaptive optics elements, Fresnel prisms, lenses, mirrors, liquid crystal elements, prisms or any combination thereof. One or more pieces which is selected from the first and/or the second pieces is interchangeable after surgery, and one or more pieces is selected from the first and/or the second pieces, that comprises of one or more means of fixation into the eye.

It is also in the scope of the invention wherein least one of the aforesaid mirrors is made of dielectric material or any other vaporized material.

It is also in the scope of the invention wherein a biocompatible coating layer coats (i) at least part of the implant as defined in any of the above; (ii) at least part of the aforesaid at least one mirror, or both (i) and (ii).

It is also in the scope of the invention wherein the optical arrangement forms, in either discrete or simultaneous manner, at least two light paths. Each path is reflected by at least one mirror being different from the other. Each path and mirror forms different magnification of the image. It is according to one embodiment of the invention wherein the optical arrangement additionally comprises at least one lens. The lens is possibly selected from a group consisting inter alia of intra ocular, an external lens to the eye, or a contact lens. The at least one additional lens is possibly comprises of at least one member of a group consisting inter alia of diffractive optics element, liquid crystal element, prism or Fresnel prism. The one or more elements are possibly located on at least a portion of the body member's interior, anterior surface, posterior surface or a combination thereof, such that changes of the additional lens cause changes in light path and therefore changes in magnification.

Another object of the invention is to disclose an intra ocular implant for implantation in the interior of a human eye. The implant comprises of (a) a body member having optical properties; and, (b) an optical arrangement adapted to form at least one image on the retina. The arrangement comprises of a body member and at least one means selected in a non-limiting manner from a group consisting of diffractive optics elements, adaptive optics elements, Fresnel prisms, lenses, mirrors, prisms, liquid crystal elements or any combination thereof. The optical arrangement is possibly adapted to form one magnified image on the retina for patients with a diseased central retina.

It is also in the scope of the invention wherein at least one of the mirrors has at least one of the following shapes: aspheric shape, irregular shape, multifocal shape, fisheye shape, changing shape and a shape that corrects higher order optical aberrations.

It is also in the scope of the invention wherein the at least one mirror is mechanically attached to or vaporized on the anterior and/or posterior surfaces of the implant. It is according to one embodiment wherein the implant's surface is characterized by any predetermined shape, and comprised of the mirror coating a member selected in a non-limiting manner from a group consisting of niche, hole, depression or a combination thereof.

It is also in the scope of the invention wherein an intra ocular implant is disclosed. The implant adapted for positioning of a fixation into the eye. The fixation is selected in a non-limiting manner from the group consisting of lens capsular bag fixation and iris supported fixation.

It is also in the scope of the invention wherein a secondary intraocular implant is disclosed, and is especially useful for implantation into a psuedophakic eye. The implant is adapted e.g., for a positioning of fixation into said eye. The fixation is selected in a non-limiting manner from a group consisting of anterior chamber fixation, posterior chamber fixation, capsular bag fixation, scleral fixation, intra-vitreous fixation, sulcus fixation, iris supported fixation and a loop facilitated fixation which may be characterized by (i) at least part of at least one loop is utilized for fixation in the capsular bag; and (ii) at least part of said implant's body member is placed outside the lens capsular bag.

It is also in the scope of the invention wherein the implant comprises of at least one first piece and at least one second piece. The first piece comprises of at least one mirror. The piece is possibly interchangeable after surgery. The at least one second piece comprises of means of fixation.

It is also in the scope of the invention wherein at least one of the mirrors is made of dielectric material or any other vaporized material.

It is also in the scope of the invention wherein a biocompatible coating layer coats (i) at least part of said implant; (ii) at least part of said at least one mirror, or both (i) and (ii).

It is also in the scope of the invention wherein the optical arrangement forms in either discrete or simultaneous manner at least two light paths. Each path reflected by at least one different mirror than the other. Each path and mirror forms different magnification of said image. It is according to one embodiment wherein the optical arrangement additionally comprises of at least one lens. The lens is selected in a non-limiting manner from a group consisting of intra ocular, an external lens to the eye, or a contact lens. The at least one additional lens comprises of at least one member of a group consisting of diffractive optics element, liquid crystal element, prism or Fresnel prism; said one or more elements are located on at least a portion of said body member's interior, anterior surface, posterior surface or a combination thereof, such that changes of said additional lens cause changes in light path and therefore changes in magnification.

It is also in the scope of the invention wherein at least part of the implant is at least partially located under the iris.

Another object of the invention is to disclose an intra ocular implant. The implant comprises (a) a body member; and, (b) an optical arrangement comprising at least one mirror and, especially an arrangement comprising at least one member of a group consisting of lens, prisms, diffractive optics elements, liquid crystal elements, Fresnel prisms, and adaptive optics elements. The at least one mirror is operationally connected to the action of the ciliary muscle or to it's effect on the zonules and capsule of the natural lens. The mirror is possibly adapted to change curvature, position or optical properties, such that bringing objects into focus is facilitated in presbyopic patients.

Another object of the invention is to disclose an intra ocular implant which comprises of (a) a body member having optical properties; and, (b) an optical arrangement comprising at least one mirror and at least one member selected from a group consisting of lens, liquid crystal element, prisms, diffractive optics elements, Fresnel prisms and adaptive optics elements. The optical arrangement is adapted for forming a plurality of images originating from a plurality of objects, objects being at varying distances from the eye, said images focused on the retina of a presbyopic patient.

Another object of the invention is to disclose an intra ocular implant. This implant comprises of a body member having optical properties, comprising at least two diffractive optics elements or at least two Fresnel prisms. The elements are possibly located in a part of the implant; this part is selected from the interior, anterior surface or posterior surface. The elements covers wholly or partially said parts, The diffractive optics elements or Fresnel prisms are adapted to form at least one magnified image on the retina; at least a portion of the image comprising at least one part of the central visual field; and optionally, one or more of images comprising at least part of the peripheral visual field.

Another object of the invention is to disclose a lens assembly. This assembly comprises of (a) an intra ocular lens containing a body member, said body member comprising, at least in part, of light polarizing material, implanted in a location selected from a group consisting of the anterior chamber, posterior chamber, sulcus or capsular bag of the eye; and, (b) an external or contact lens comprising at least in part of light polarizing material. The assembly is at least partially polarizes at least part of the central visual field, at least part of the peripheral visual field or both in any angle; said external or contact lens are adjustable by the patient so as to control the measure of light striking the retina in any part of the retina.

Finally, it is an object of the invention to disclose an intra ocular implant useful for improving the vision of a patient in which future development of retinal disorders may occur. The implant comprises of a body member having optical properties; and an optical arrangement adapted to form at least one image on the retina. The arrangement comprises a body member and at least one means selected from a group consisting of diffractive optics elements, adaptive optics elements, Fresnel prisms, lenses, liquid crystal elements, mirrors, prisms or any combination thereof. The optical arrangement has at least one mirror located beneath the iris out of the visual axis and optionally comprises at least one additional lens, selected from a group consisting of intra ocular lens, an external lens to the eye, or a contact lens. The at least one additional lens comprises at least one member of a group consisting of diffractive optics element, liquid crystal element, prism or Fresnel prism such that the additional lens is adapted to divert light through the at least one mirror located beneath the iris, so as to form at least one magnified central image on the retina and optionally at least one peripheral image.

BRIEF DESCRIPTION OF THE EMBODIMENTS

Figure 1B:
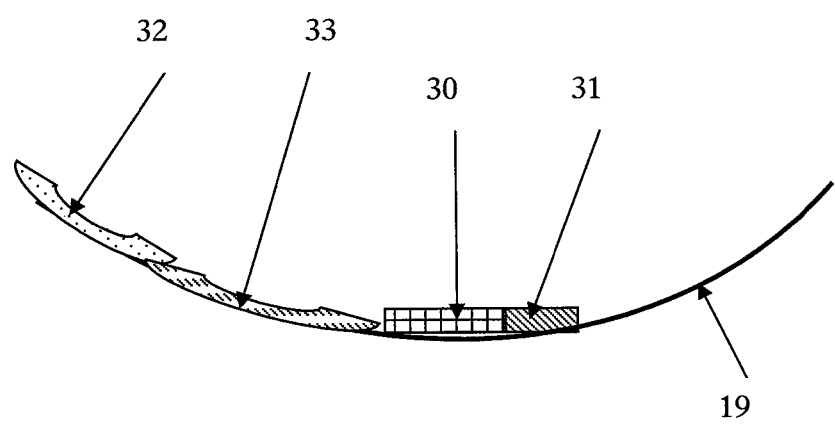
Figure 2A:
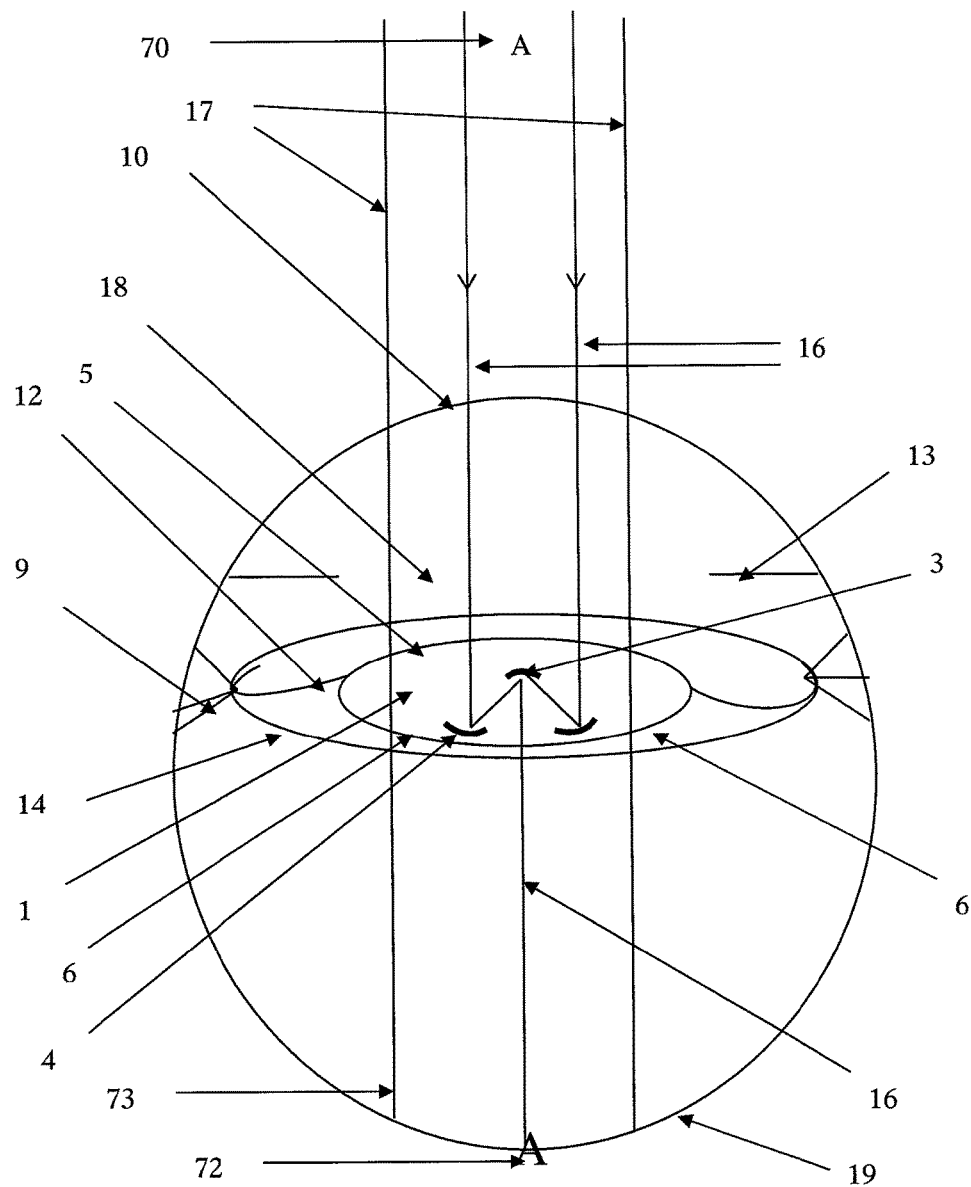
Figure 2B:
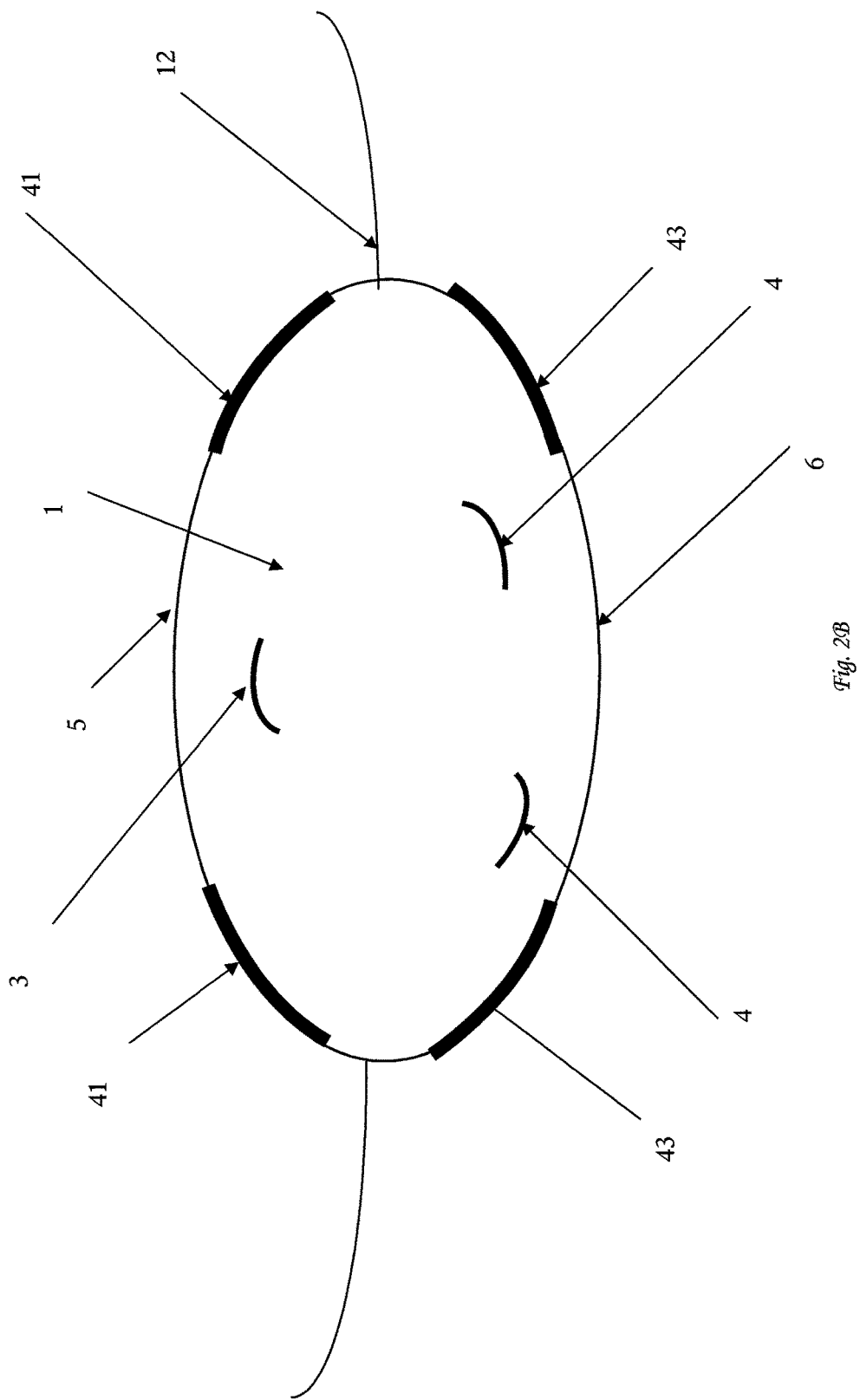
Figure 3:
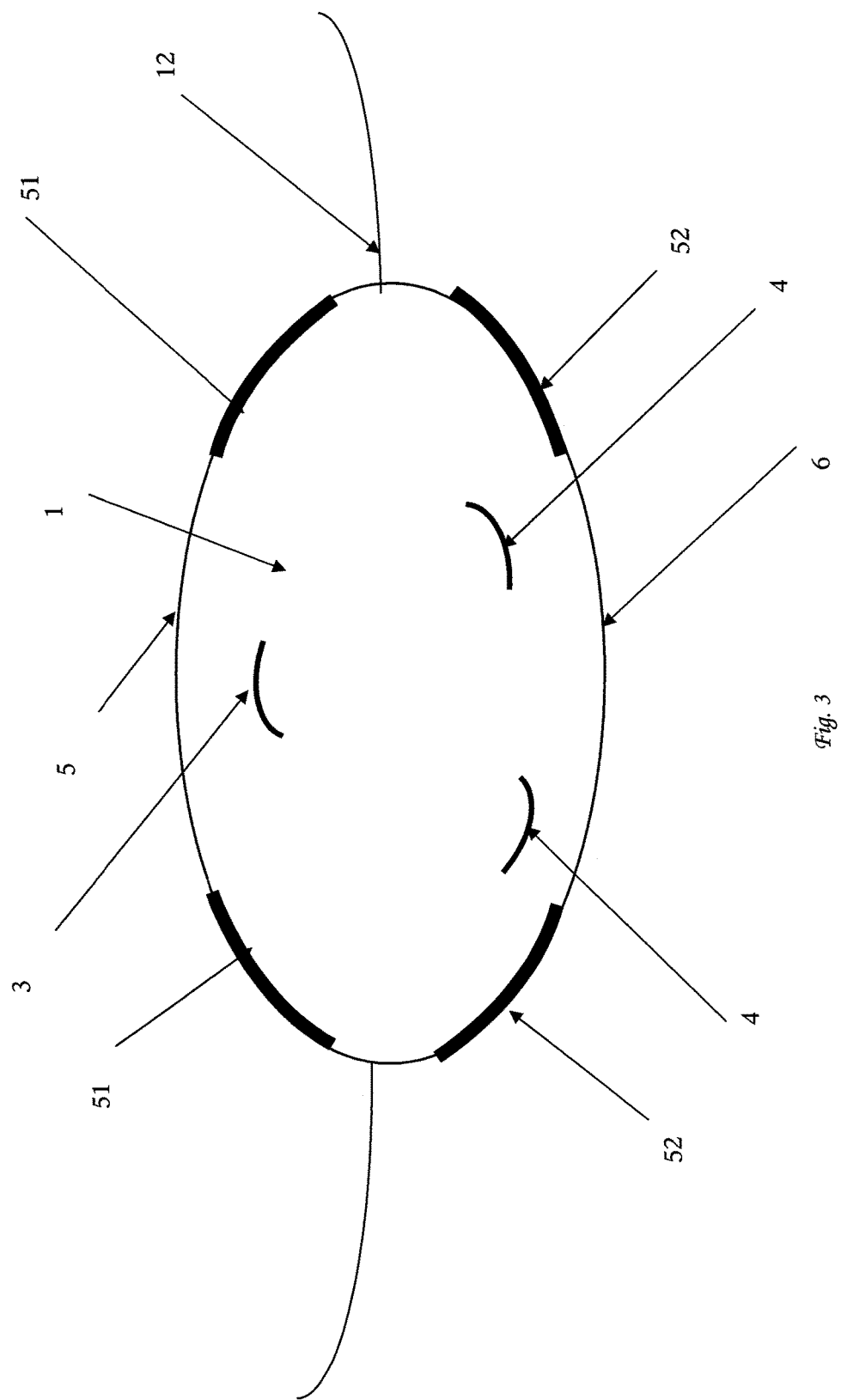

In order to understand the invention and to see how it may be implemented in practice, preferred embodiments will now be described, by way of non-limiting example only, with reference to the accompanying drawings in which FIG. 1A presents a schematic vertical illustration of the image received on the retina according to one embodiment of the present invention;

FIG. 1B presents a schematic side view of the image received on the retina according to one embodiment of the present invention;

FIG. 2A presents a schematic illustration of perceivable color differences received on the retina according to one embodiment of the present invention;

FIG. 2B presents a schematic illustration of perceivable color differences received on the retina according to another embodiment of the present invention;

FIG. 3 presents a schematic illustration of overlap and/or illumination reduction according to one embodiment of the present invention.

Figure 4:
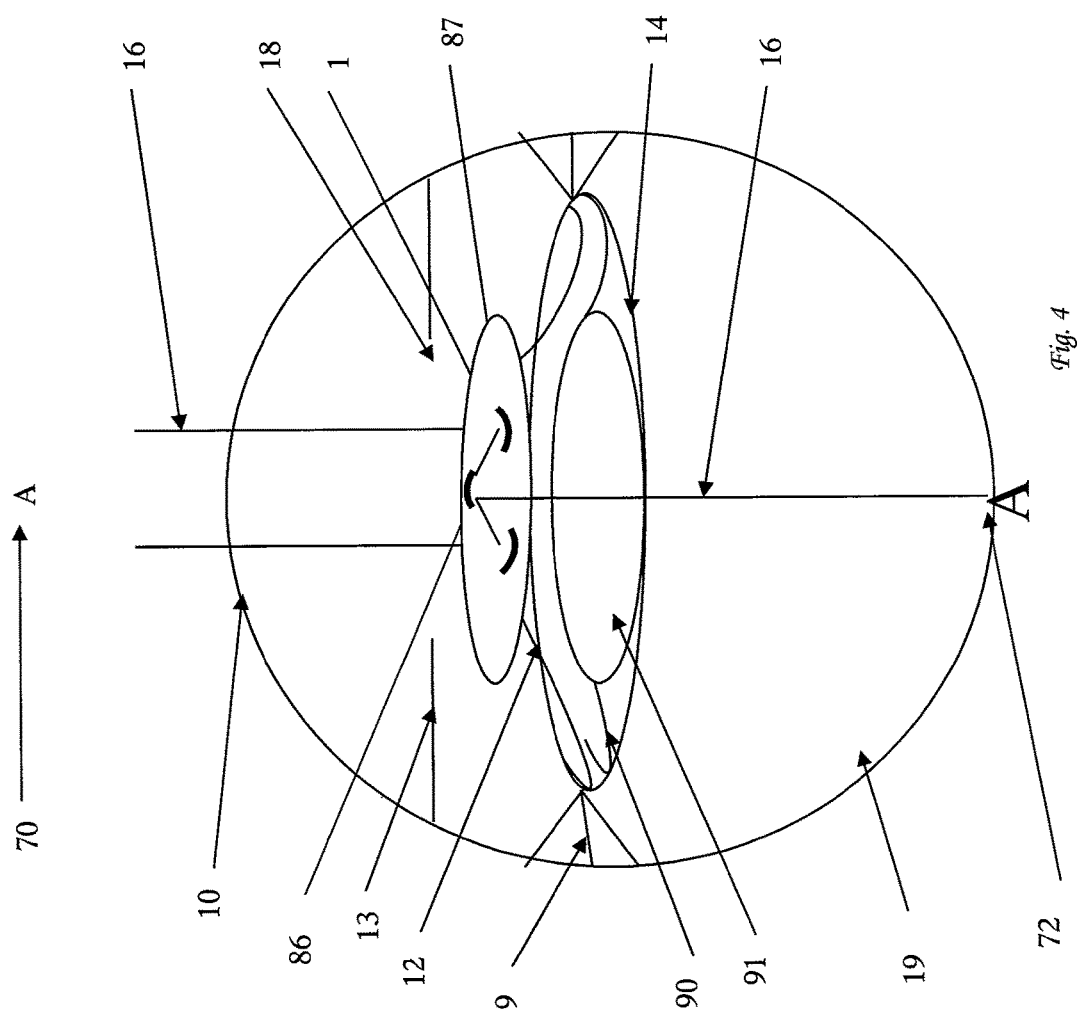
Figure 5:
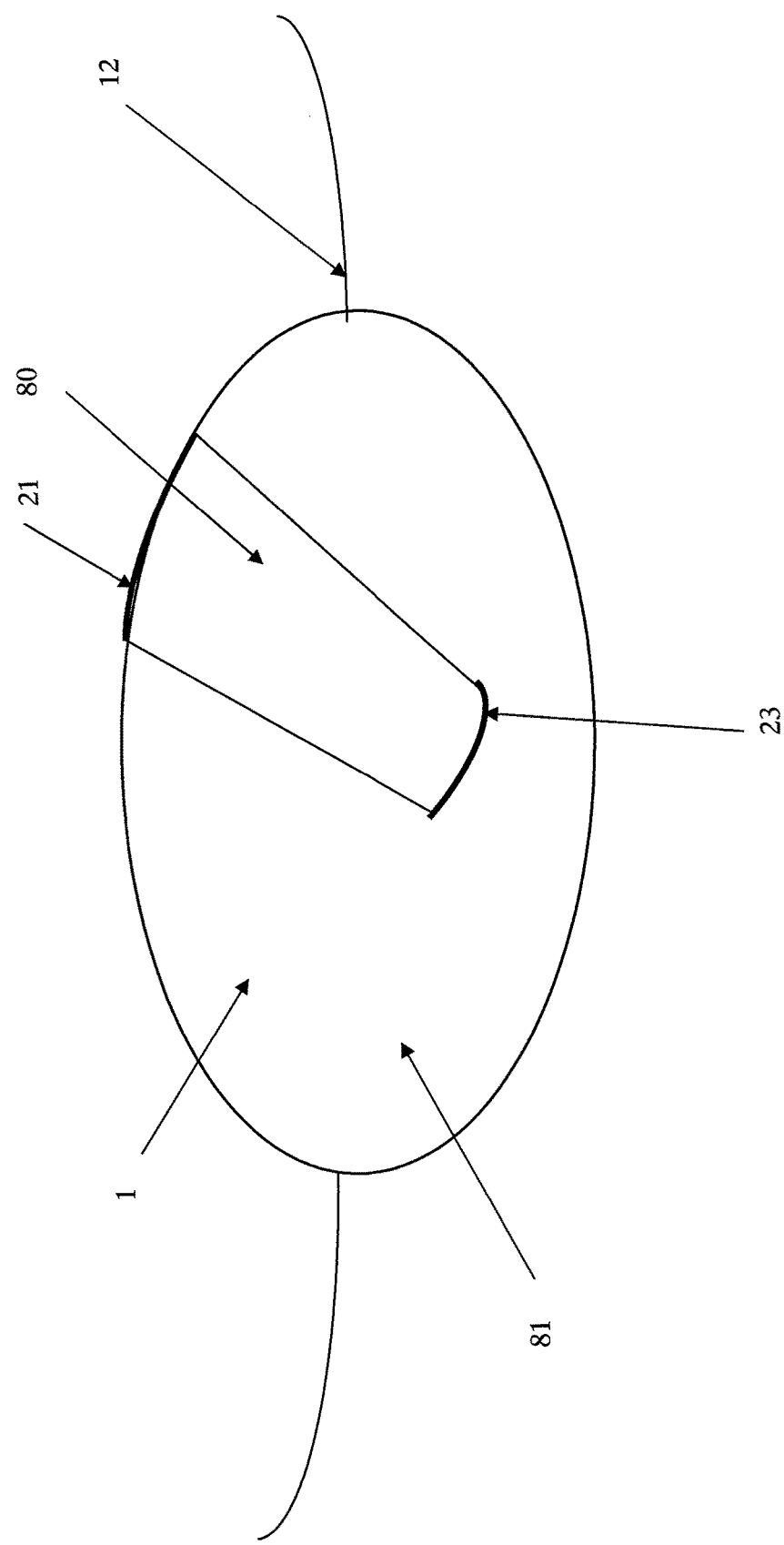
Figure 6:
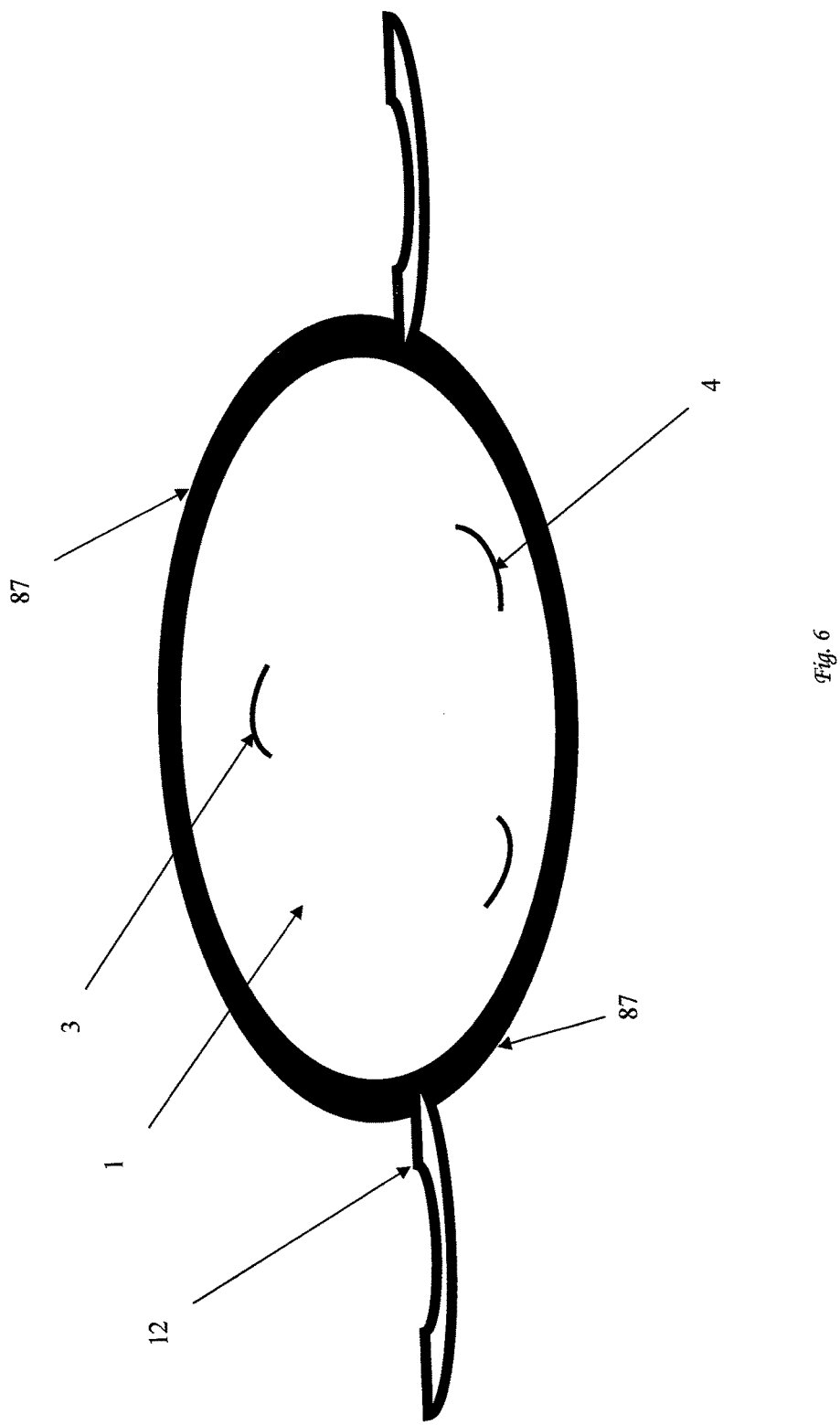
Figure 7:
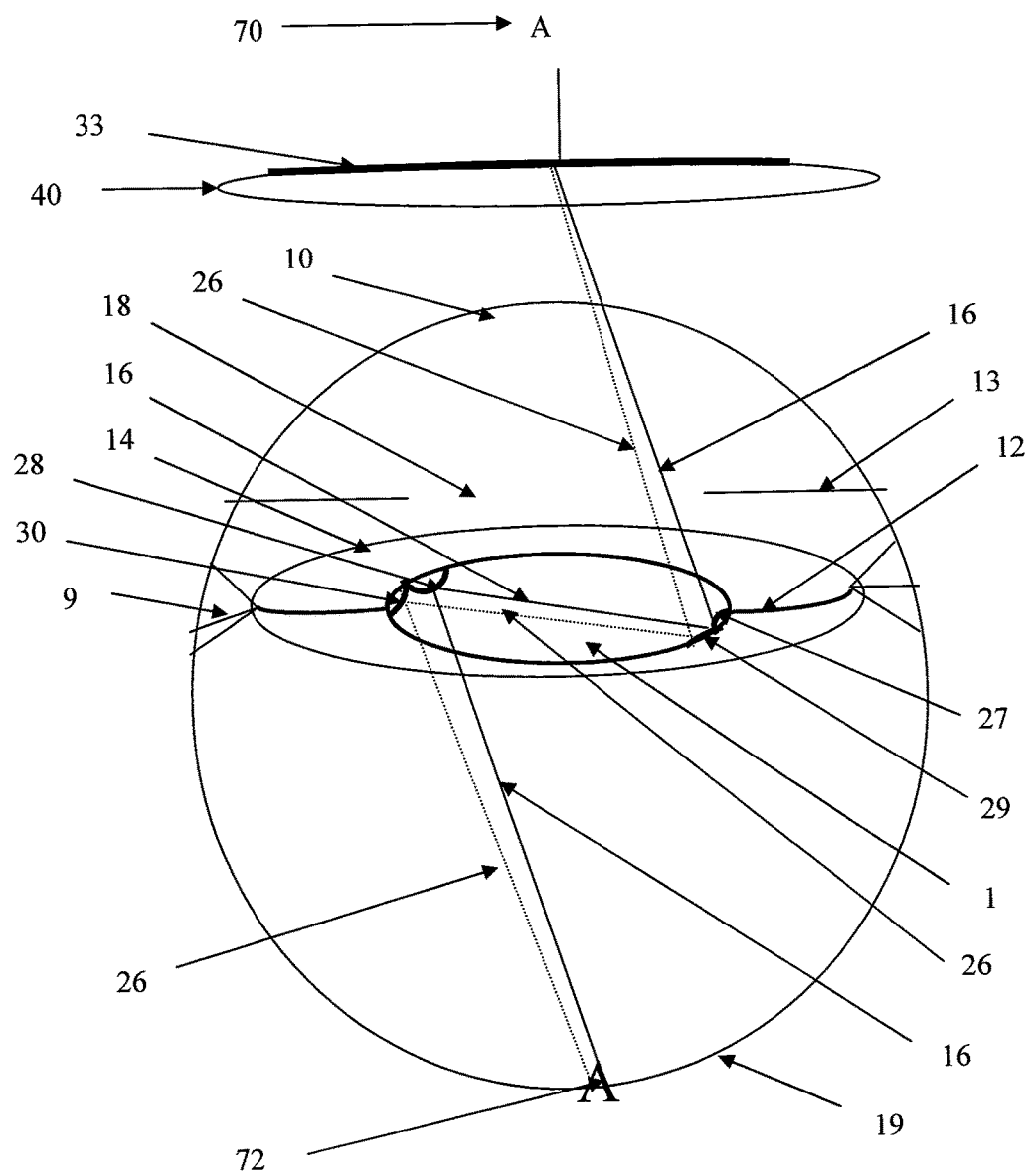
Figure 8:
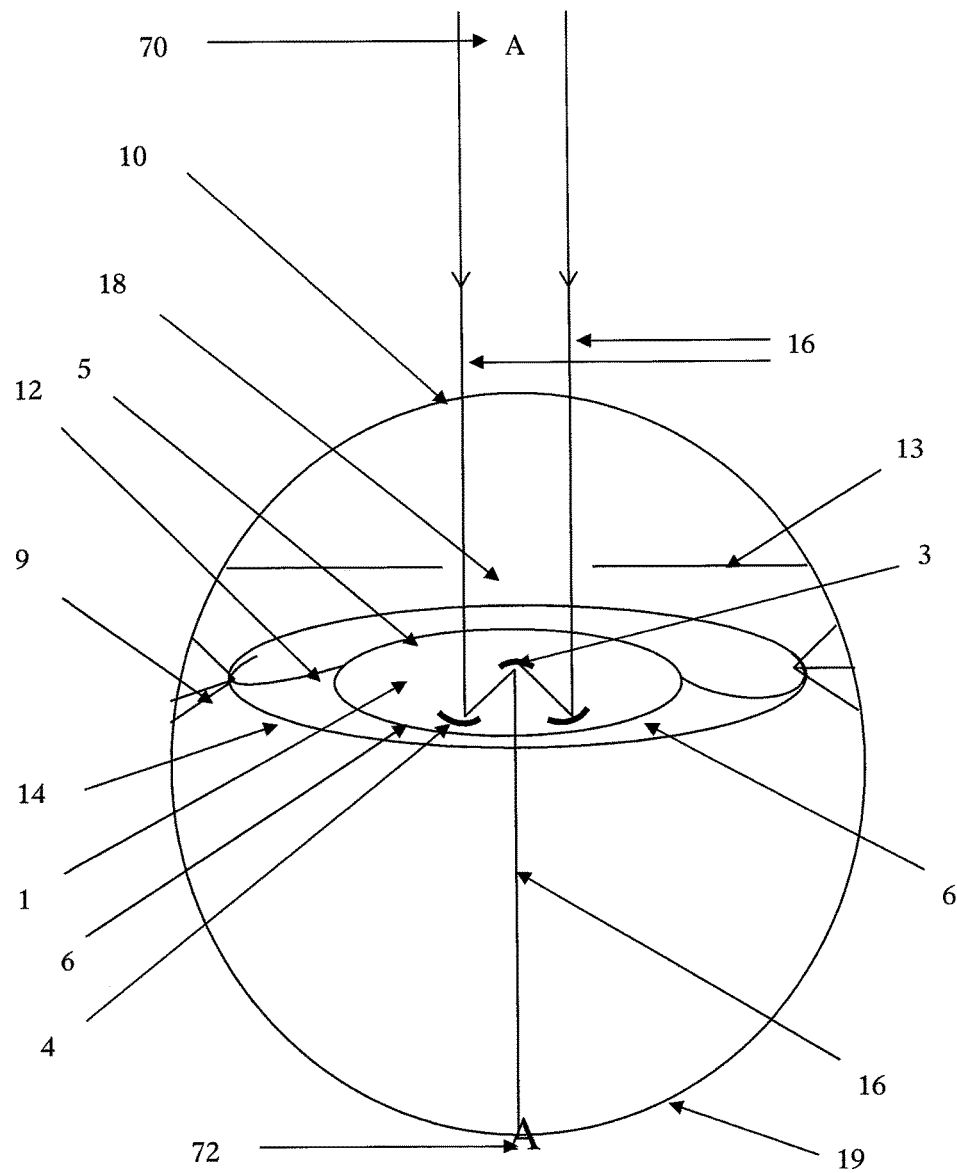
Figure 9:
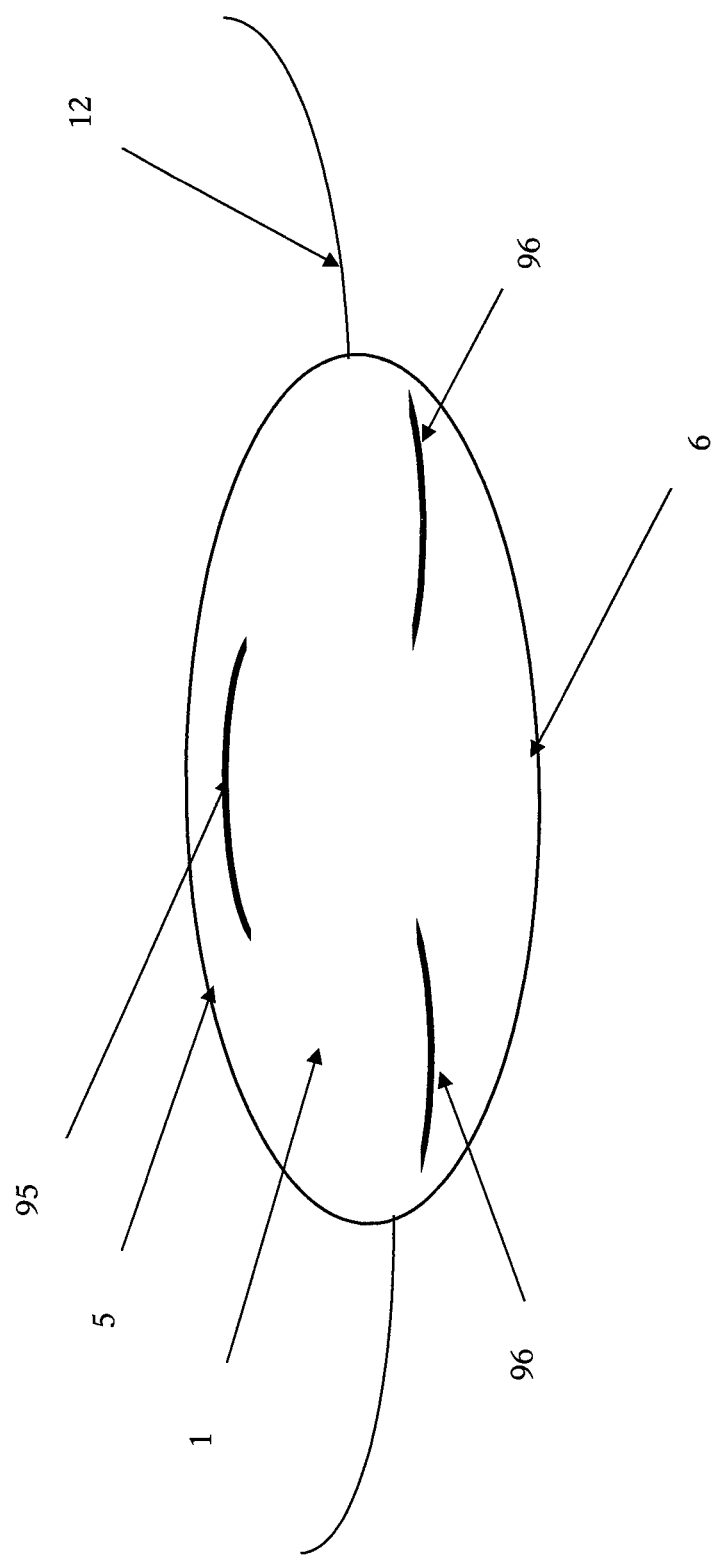
Figure 10A:
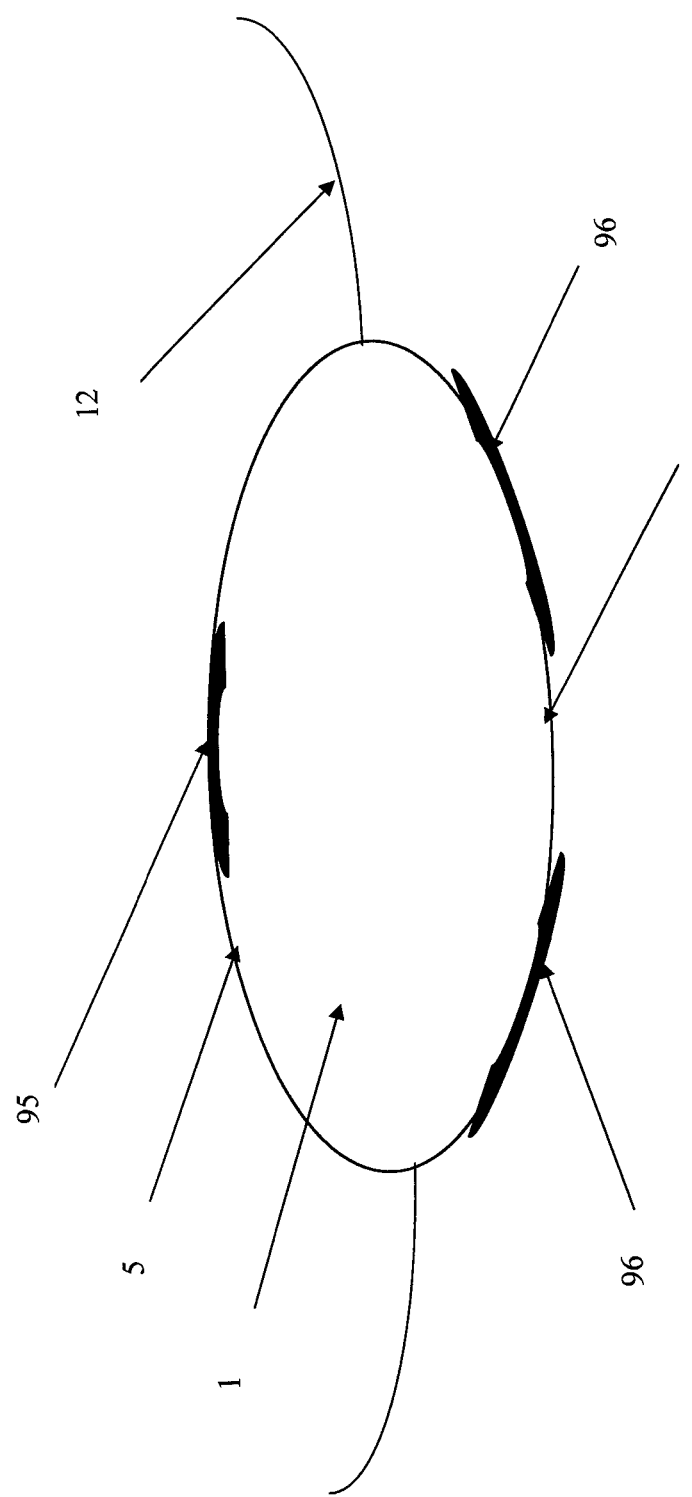
Figure 10B:
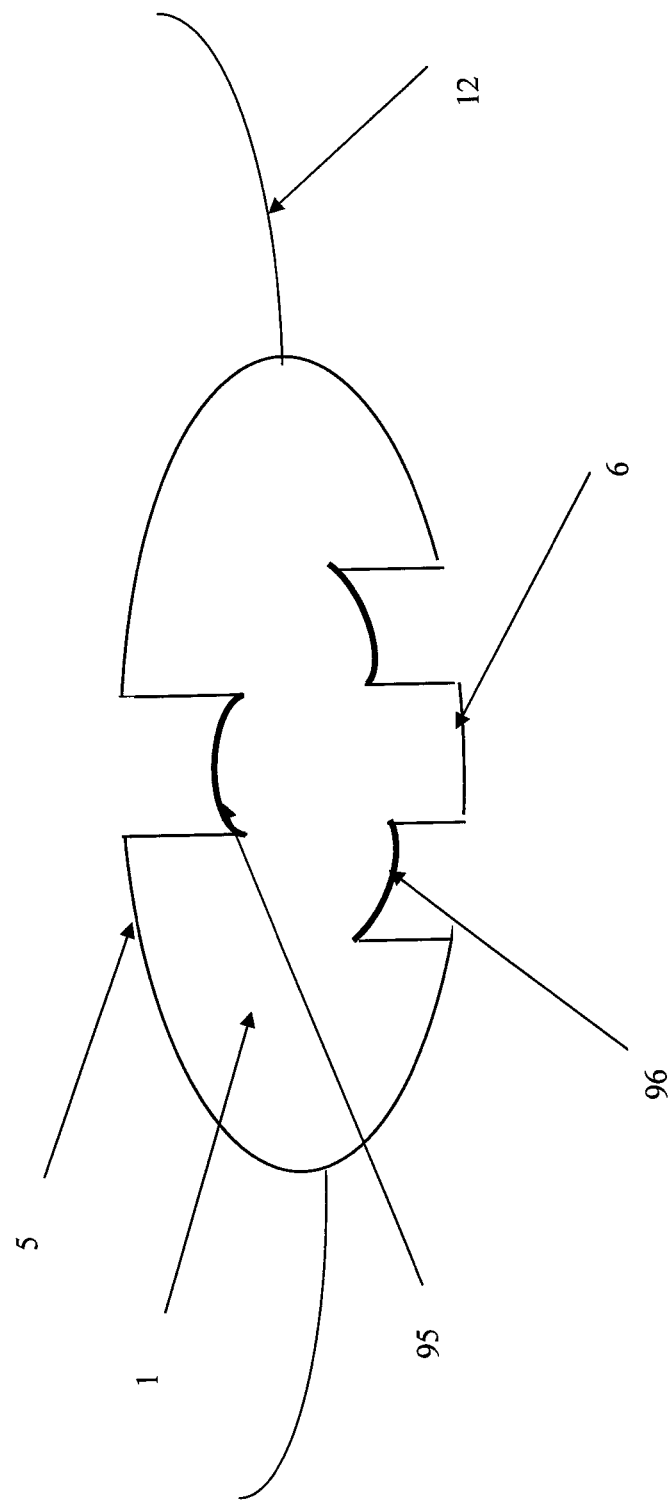
Figure 11:
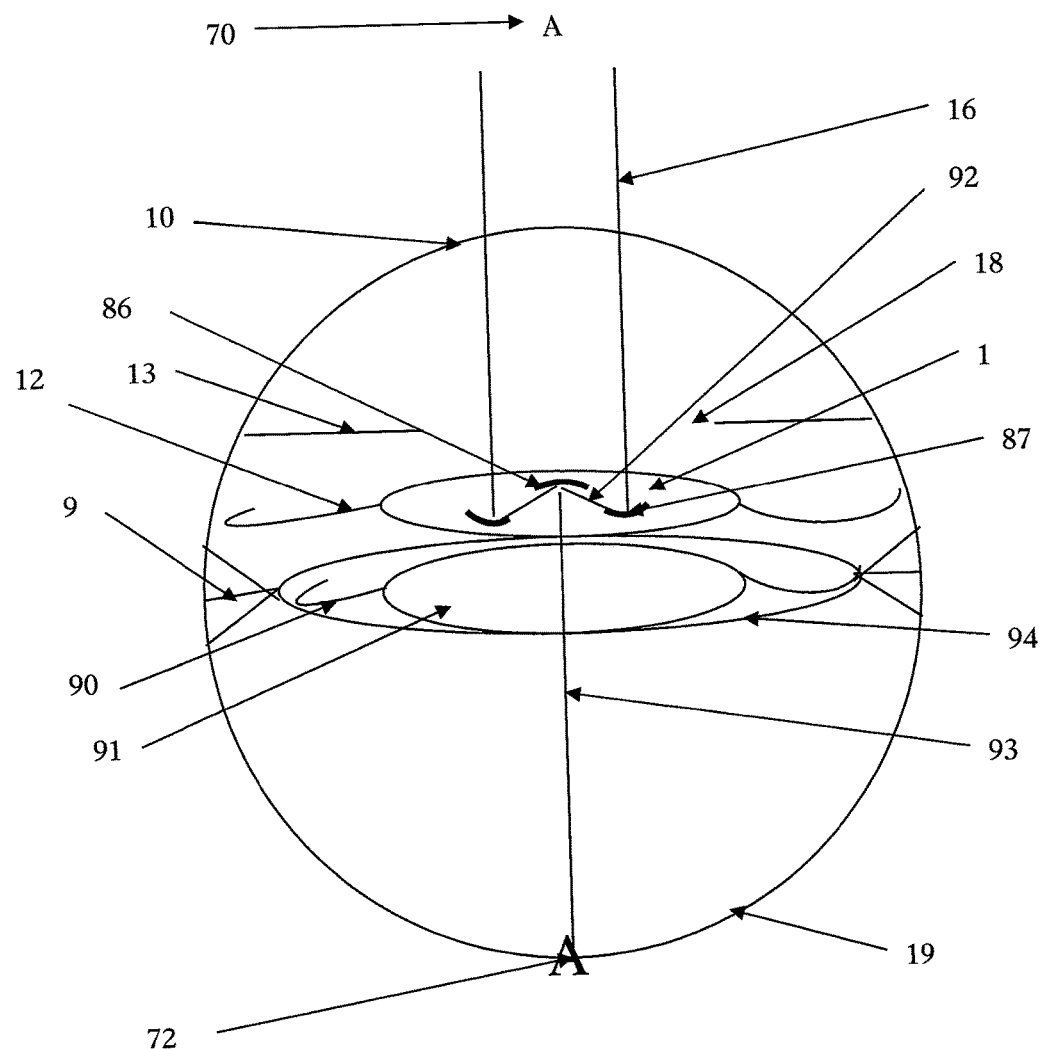
Figure 12:
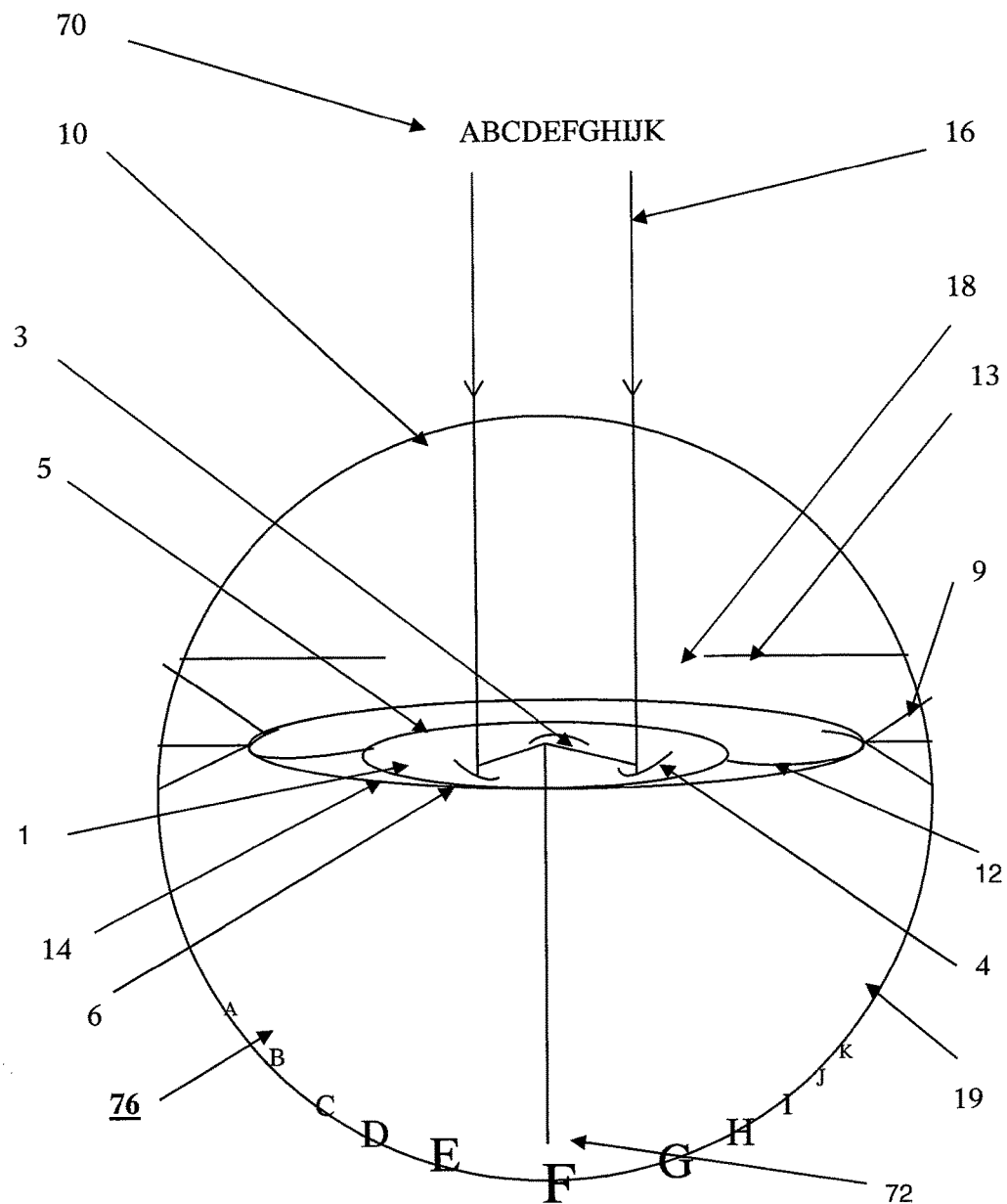
Figure 14A:
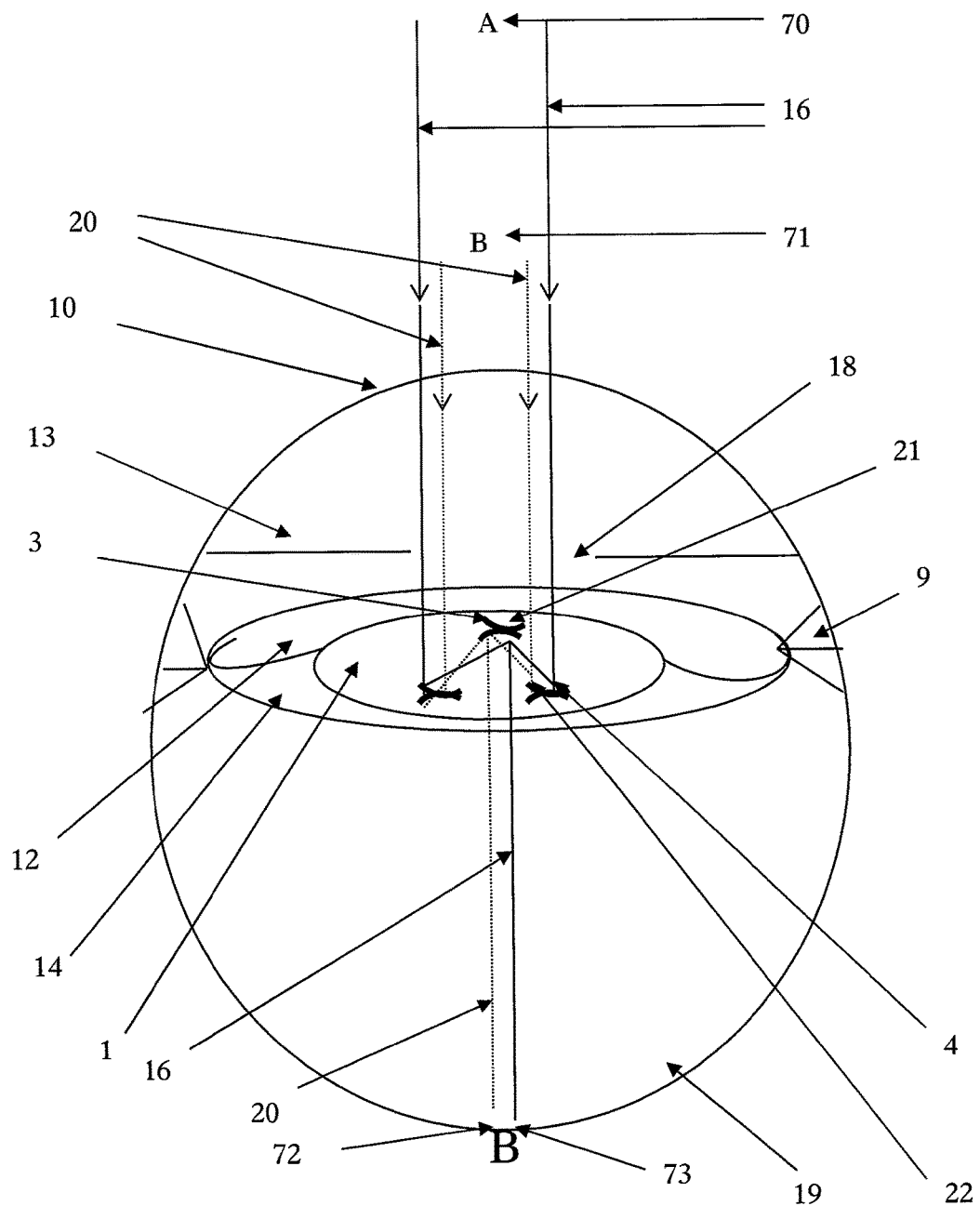
Figure 14B:
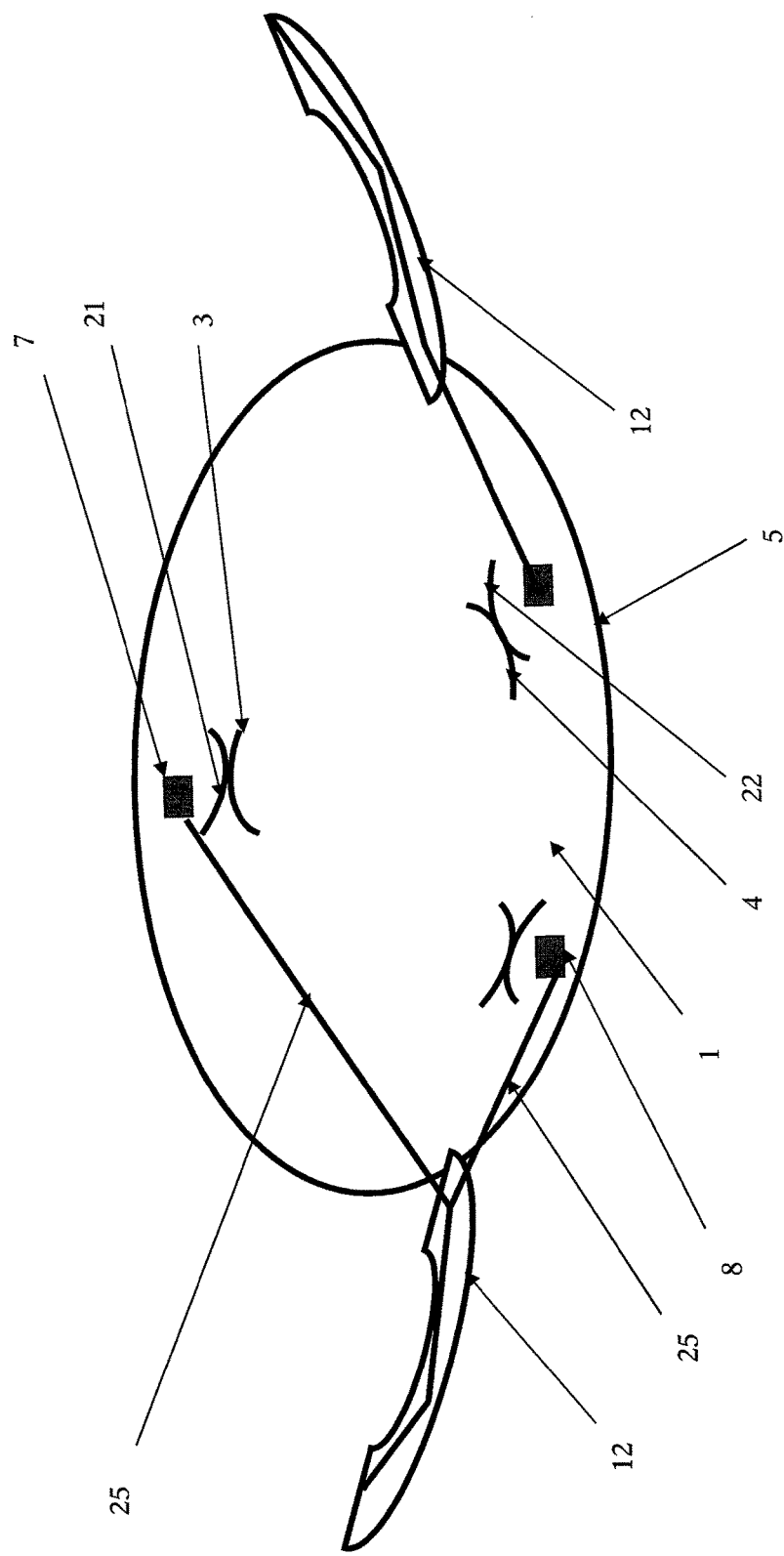
Figure 15:
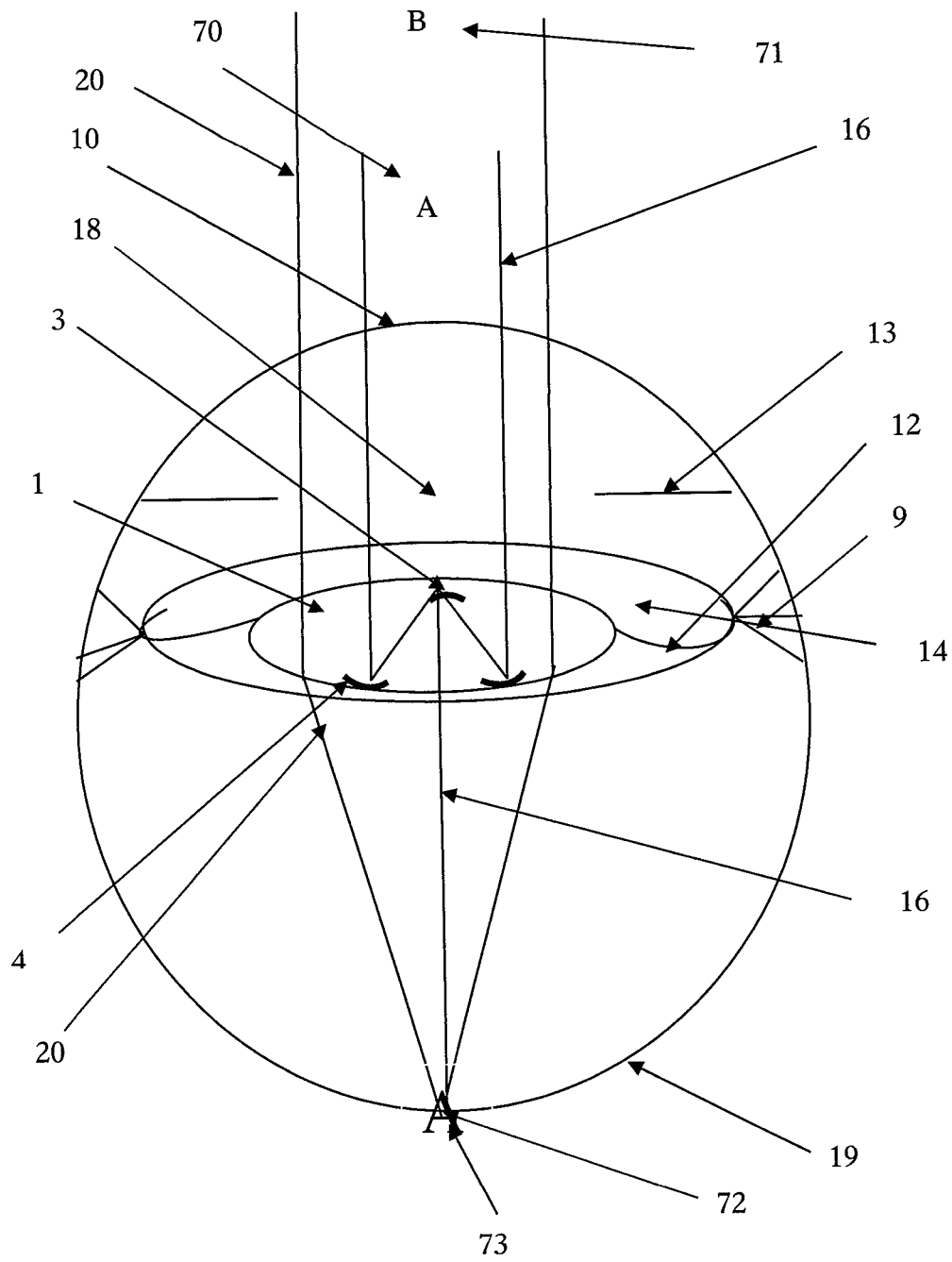
Figure 16A:
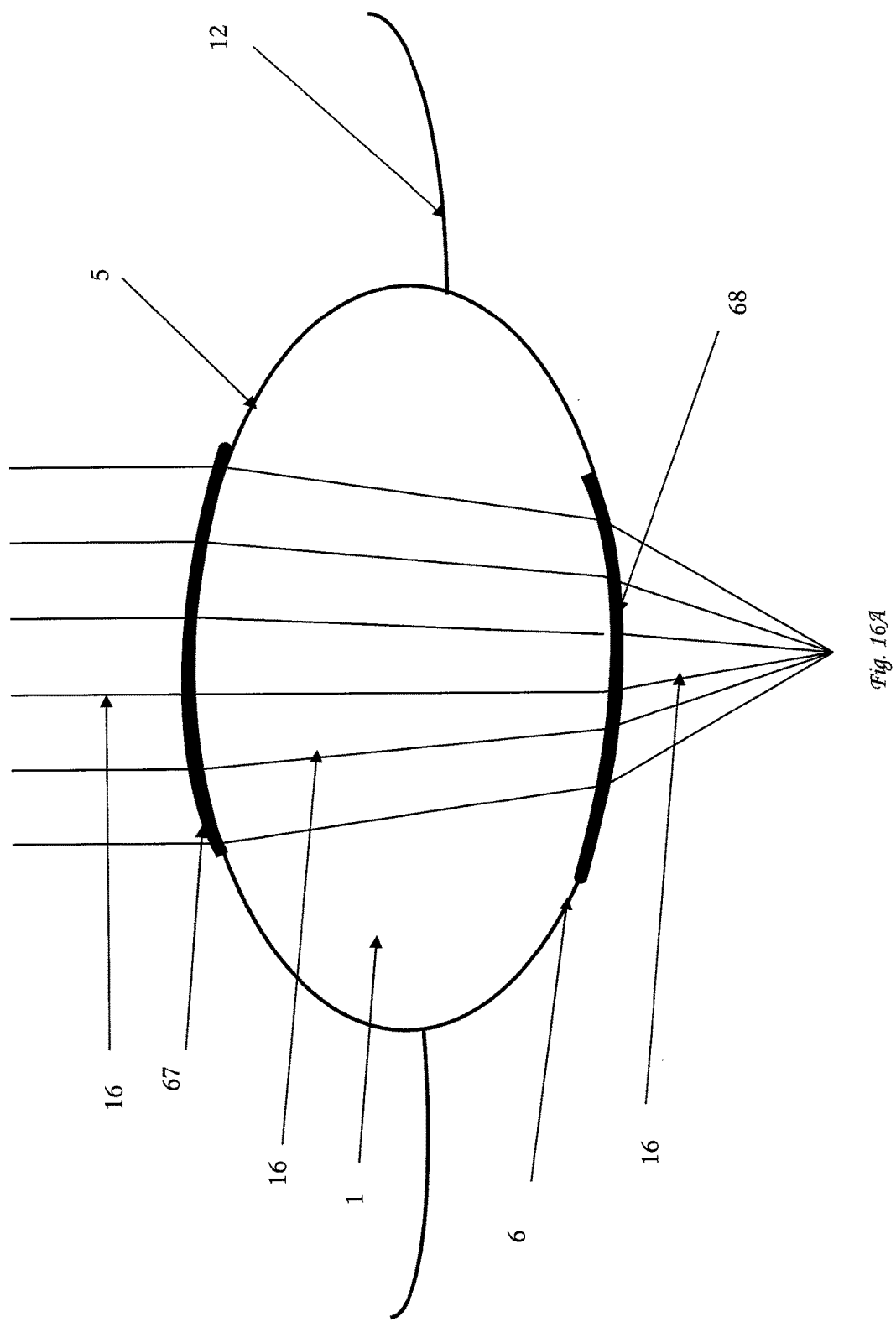
Figure 17:
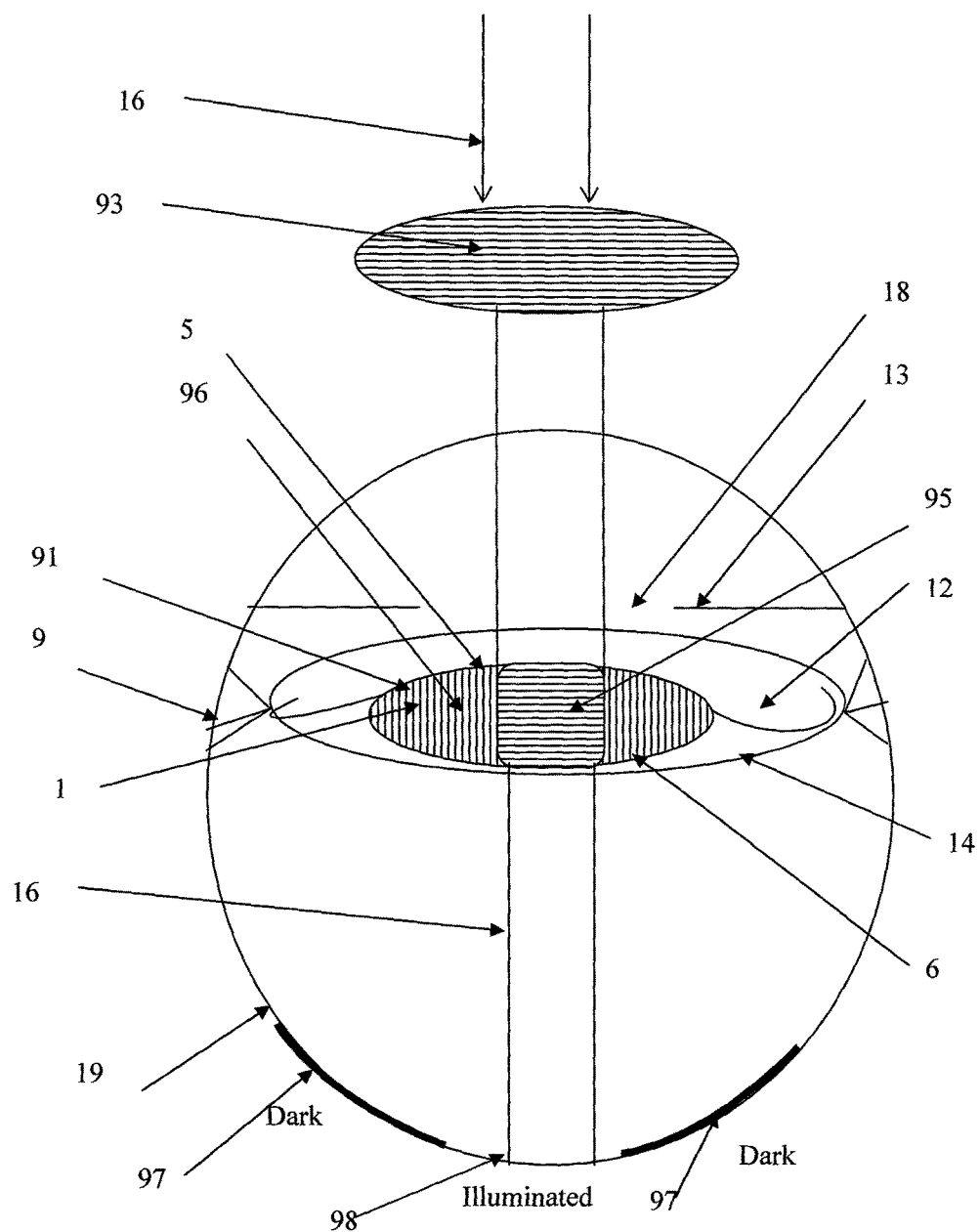

FIG. 4 presents a schematic illustration of a secondary intra ocular implant according to one embodiment of the present invention;

FIG. 5 presents a schematic illustration of an intra ocular implant made up of at least two pieces according to one embodiment of the present invention;

FIG. 6 presents a schematic illustration of an intra ocular implant with a biocompatible coating according to one embodiment of the present invention;

FIG. 7 presents a schematic illustration of an optical arrangement with more than one light path according to one embodiment of the present invention;

FIG. 8 presents a schematic illustration of an implant partially under the iris according to one embodiment of the present invention;

FIG. 9 presents a schematic illustration of an implant with aspheric mirrors according to one embodiment of the present invention FIG. 10A presents a schematic illustration of an implant with mirrors attached to the surface according to one embodiment of the present invention;

FIG. 10B presents a schematic illustration of an implant with mirrors attached to a niche or hole according to one embodiment of the present invention;

FIG. 11 presents a schematic illustration of a secondary intraocular implant with mirrors implanted into a psuedophakic eye according to one embodiment of the present invention;

FIG. 12 presents a schematic illustration of an implant with mirrors in a fisheye configuration according to one embodiment of the present invention;

FIG. 13 A presents a schematic illustration of an implant with movable mirrors according to one embodiment of the present invention;

FIG. 13 B presents a schematic illustration of an implant with movable mirrors according to another embodiment of the present invention;

FIG. 14A presents a schematic illustration of an implant with variable curvature mirrors according to one embodiment of the present invention;

FIG. 14 B presents a schematic illustration of an implant with variable curvature mirrors according to another embodiment of the present invention;

FIG. 15 presents a schematic illustration of an intra ocular implant for implantation into a presbyopic eye according to one embodiment of the present invention;

FIG. 16A presents a schematic illustration of an intra ocular implant with two optical elements according to one embodiment of the present invention;

FIG. 16B presents a schematic illustration of an intra ocular implant with two optical elements according to another embodiment of the present invention; and, FIG. 17 presents a schematic illustration of an intra ocular implant provided with light polarizing material according to one embodiment of the present invention.

Figure 18:
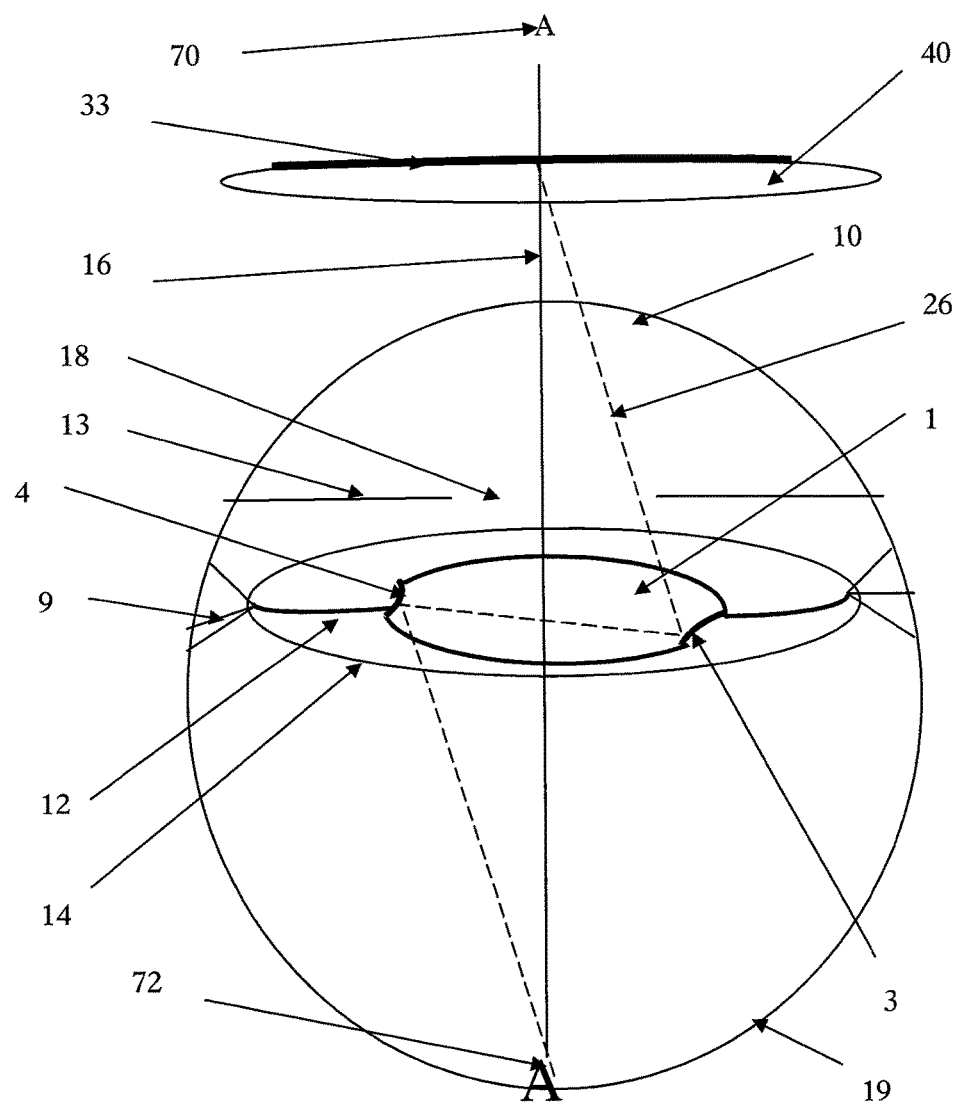

FIG. 18 presents a schematic illustration of an intra ocular implant with mirrors hidden beneath the iris according to another embodiment of the present invention.

DETAILED DESCRIPTION OF THE PREFERRED EMBODIMENTS

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a means to improve the vision of patients suffering from retinal diseases and/or presbyopia.

The term "AMD" hereinafter refers to age-related macular degeneration. The term "other retinal diseases" hereinafter refers to inherited, degenerative and inflammatory diseases that affect the center of the retina or the periphery of the retina.

The term "fisheye lens" refers hereinafter to a wide-angle lens that takes in a wide, hemispherical image, and the lens referred to may be either circular or full frame.

Coatings used in this invention are exemplified by plastics such as commercially available Parylene product in many formations, for example: Parylene A, Parylene C, etc., or any other a conformal protective polymer adapted as a coating material utilized to uniformly protection; glass ($SiO_2$) or a combination thereof or any other biocompatible material.

The term "Psuedophakic or Pseudophakia" refers hereinafter to the substitution of the natural crystalline lens with a synthetic lens. Pseudophakic intra ocular lenses (IOL) are used in cataract surgery.

The term "Dielectric coating" refers to a type of a mirror composed of multiple thin layers of dielectric material, or deposited by means of vaporisation on a substrate of glass or some other optical material.

In the figures below where applicable: intra ocular implant is 1, with anterior surface 5 and posterior surface 6, the lens capsular bag is 14, the iris is 13, the zonules are 9, the pupil opening is 18, the retina is 19, the cornea is 10, the intraocular implant's fixation loops are 12, the object is 70, the image on the retina is 72 and the central light going through the optical system is 16.

Reference is now made to FIGS. 1A and 1B presenting a non-limiting example of an implant with more than one central visual field 30 and 31 and more than one peripheral visual field 32 and 33 on retina 19. FIGS. 2A and 2B are a non-limiting example of perceivable differences in color between the at least two images, enabling the patient to differentiate between said visual fields. The current configuration includes other perceivable differences on the basis of criteria such as contrast, location, transmitted light spectra, magnification, illumination and focus that are not demonstrated herein. FIGS. 2A and 2B show different colors between central image 72 and peripheral image 73 of the retina 19. In FIG. 2A differences are due to the mirrors 3 and 4 and central light 16 creates different color than peripheral light 17 and in FIG. 2B differences are due to elements 41 and 43, which may be diffractive optics elements, Fresnel prism, or other prism on the anterior surface 5, posterior surface 6 or the interior of the implant 1.

Reference is now made to FIG. 3 presenting a non-limiting example of an intra ocular implant provided with means of decreasing the overlap and/or decreasing the differences in illumination between the at least two images on the retina, at least one being the central image and at least the other being the peripheral image. Diffractive optics element, liquid crystal element, Fresnel prism, or prism are 51 and 52 and mirrors are 3 and 4.

Reference is now made to FIG. 4 presenting a non-limiting example of a secondary intra ocular implant 1 with optical properties that changes the central visual field. Said lens is adapted for implantation into a psuedophakic eye. The implant 1 is shown with mirrors 86 and 87 and fixation loops 12 that are partially inside the capsular bag, while the implant 1 is at least partially outside the capsular bag 14. The artificial lens 91 with loops 90 was implanted in a cataract surgery on a prior occasion.

Reference is now made to FIG. 5 presenting a non-limiting example of an intra ocular implant made up of at least two pieces. One piece, 80, containing at least one optical element, in this example, mirror 21 and 23 from a group including: diffractive optics elements, adaptive optics elements, Fresnel, lenses, mirrors, liquid crystal elements, and prisms. The illustration presents a two-piece implant, but obviously more than two pieces can be used to make up the implant. More than one optical element or any combination of them may be used in the implant. Piece 80 may be interchangeable after surgery. At least one piece, 81, contains means of fixation such as fixation loops 12.

Reference is now made to FIG. 6 presenting a non-limiting example of an implant 1 with mirrors 3 and 4 and fixation loops 12 coated with a biocompatible layer 87. Under the current configuration, at least one optical component (exemplified by mirrors in FIG. 6) may be coated in addition to the implant coating or instead of the implant coating. The coating is done to prevent the eye from coming into contact with hazardous and non-biocompatible materials.

Reference is now made to FIG. 7 presenting a non-limiting example of the implant 1 inside lens capsular bag 14 showing an optical arrangement forming two possible light paths. According to this example, light 16 is directed by external lens 40 with element 33 (diffractive optics, liquid crystal elements, Fresnel prism, or any other prism) and reflected by mirrors 27 and 28 creating a magnified image, 72, on retina 19. If external lens 40 is replaced by another or modified, light 26 is diverted differently and reflected by mirrors 29 and 30, which create different magnification of central image 72 on retina 19. Element 33 may be located anywhere in external lens 40 or attached to external lens 40. External lens 40 may also be mounted on glasses or a contact lens. Lens 40 may also be an additional intra ocular lens, not shown in this figure.

Reference is now made to FIG. 8 presenting a non-limiting example of an intra ocular implant 1 adapted to form one magnified image 72 on the retina 19. Implant 1 contains two mirrors 3 and 4 and, optionally, one of the following: lens, prism, liquid crystal element, diffractive optics element, Fresnel prism and adaptive optics element (not shown herein). The optical arrangement shown herein as an example is implanted in the lens capsular bag 14 and the implant 1 is partially hidden beneath the iris 13.

Reference is now made to FIG. 9 presenting a non-limiting example of implant 1 provided with aspheric mirrors 95 and 96. In this example the mirrors have an aspheric shape, but the shape can also be irregular, multifocal, fisheye shape, or a changing shape and a shape that corrects higher order optical aberrations.

Reference is now made to FIGS. 10A and 10B presenting a non-limiting example of the implant 1 which magnifies the central image, with mirrors 95 and 96 mechanically attached to or vaporized on the anterior 5 or posterior surface 6 of the implant. The implant surface may be of any shape and may include one or more mirrors coating a niche and/or hole and/or depression as exemplified in FIG. 10B.

Reference is now made to FIG. 11 presenting a non-limiting example of a secondary intraocular implant 1 with mirrors 86 and 87 implanted into a psuedophakic eye. The implant as shown is especially adapted for a position of fixation into the sulcus of the eye. The position of fixation can also be anterior chamber fixation, posterior chamber fixation, capsular bag fixation, intra-vitreous fixation, iris supported fixation or a fixation in which at least part of at least one loop is adapted for fixation in the capsular bag and at least part of said implant's body member is placed outside the capsular bag as demonstrated in FIG. 4. The artificial lens 91 with loops 90 was implanted in a cataract surgery on a prior occasion.

Reference is now made to FIG. 12 presenting a non-limiting example of the implant 1 showing mirrors 3 and 4 in a fisheye configuration. Mirrors 3 and/or 4 provide diminishing magnification from the central visual field 72 to the peripheral visual field 76 on retina 19. More than one mirror can be provided and configured in this way. Mirrors 3 and 4 can also be configured to create an opposite effect of diminishing magnification from a magnified periphery of an image to a less magnified center of an image.

Figure 13A:
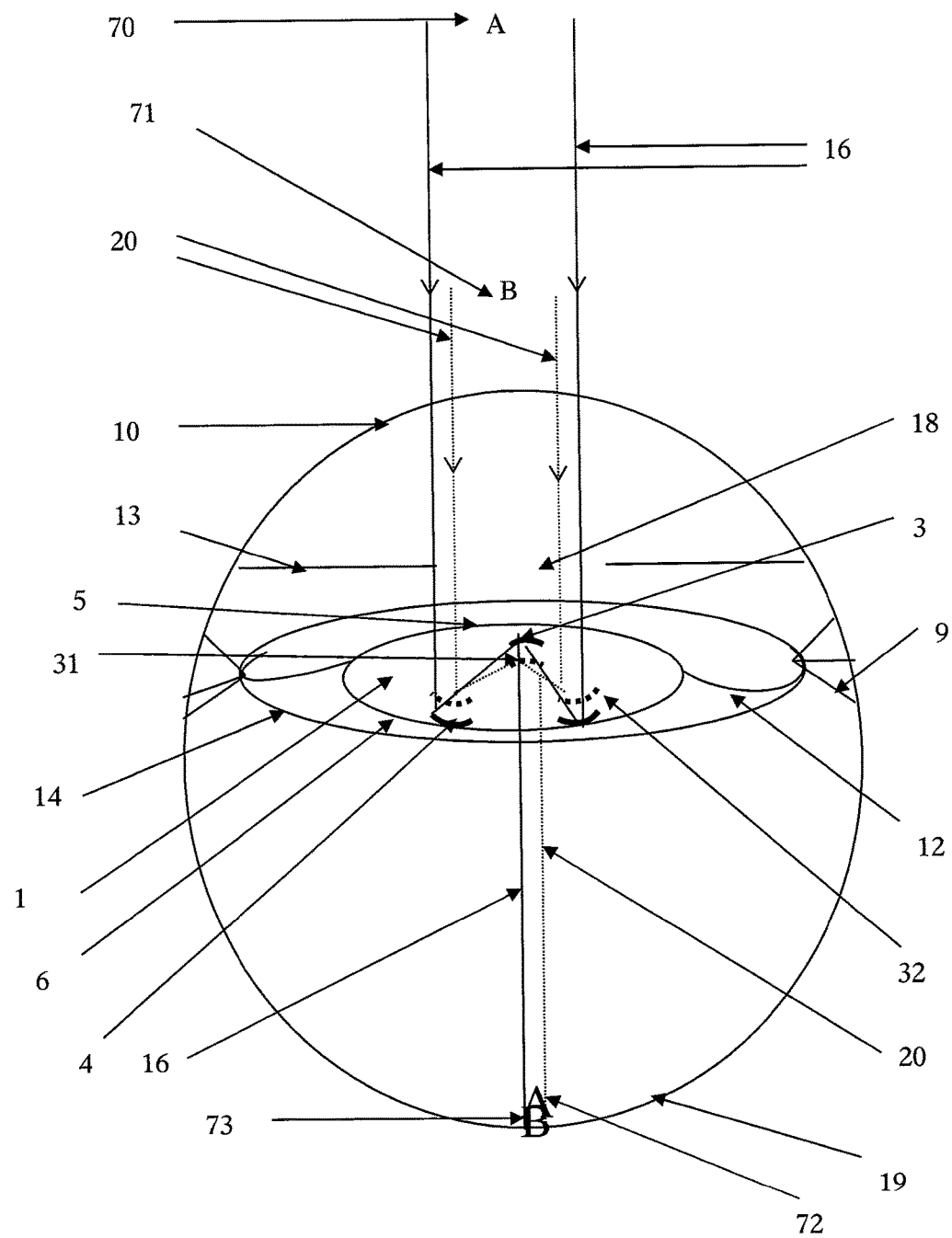
Figure 13B:
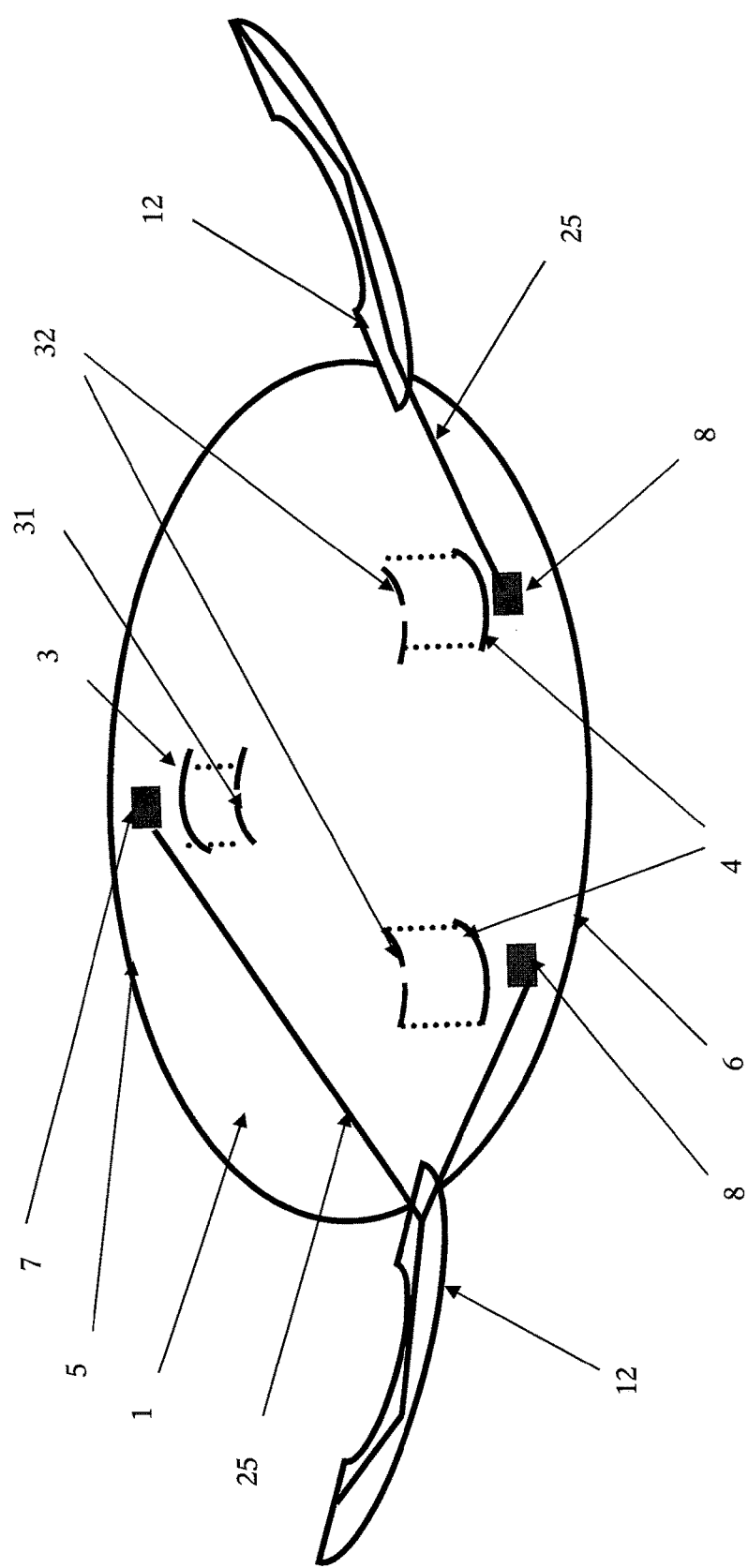

Reference is now made to FIGS. 13A and 13B presenting a non-limiting example of the intra ocular implant 1 with mirrors 3 and 4. The mirrors 3 and/or 4 are operationally connected to the action of the ciliary muscle or to its effect on the zonules 9 and the lens capsular bag 14. In FIGS. 13A and 13B the mirrors are adapted to change their position from 3 to 31 and from 4 to 32; light 16 is focused on the retina for distance and light 20 for near. Elements 7 and/or 8, which may be connected through connector 25 as shown in FIG. 13B may be used to change the position of the mirrors. The change in position changes the focus on the retina from a distant object 70 focused as image 72 on retina 19 to a near object 71 focused as 73 and vice versa. This has the effect of facilitating the bringing of objects into focus in presbyopic patients.

FIGS. 14A and 14 B present a non-limiting example of implant 1 with change in curvature of mirrors 3 and/or 4 to a different shape, 21 and/or 22, light 16 is focused on the retina for distance and light 20 for near. The change in curvature changes the focus on the retina from distant object 70 focused as image 72 on retina 19 to near object 71 focused as image 73. This has the effect of facilitating the bringing of objects into focus in presbyopic patients. Elements 7 and/or 8 as shown in FIG. 14 B may be used to change the position of the mirrors.

Reference is now made to FIG. 15 presenting a non-limiting example of an intra ocular implant 1 for implantation into a presbyopic eye. Mirrors 3 and 4 are adapted to focus close object 70 and form an image 72 on the retina 19 of a presbyopic person and at least one additional image 73 is focused on the retina, originating from a more distant object 71. Light originating from a close object 70 focused on the retina is 16 and light originating from distant object 70 behind the retina is 20.

Reference is now made to FIGS. 16A and 16B presenting non-limiting examples of an intra ocular implant 1 with at least two elements 67 and 68 (diffractive optics liquid crystal elements, or Fresnel prism or other prisms). The elements are located in the anterior 5, posterior 6 or interior part of the implant. The aforementioned elements optionally cover wholly or partially the implant's surfaces. The diffractive optics elements, liquid crystal elements or fresnel elements are adapted to form at least one magnified image on the retina and, optionally, at least one image containing at least part of the peripheral visual field on the retina. FIG. 16A shows two elements 67 and 68 (diffractive optics or Fresnel prism or other prisms) on the anterior and posterior divert light at an angle as if the light was refracted by a lens. FIG. 16B shows diffractive optics element, Fresnel prism or other prisms 67 and 68 diverting light at a smaller angle as if the light was reflected by a mirror. In both cases, a magnified image is projected on the retina.

Reference is now made to FIG. 17 presenting a non-limiting example of a lens assembly comprising an intra ocular implant 1, which is composed at least in part of light polarizing material implanted in the lens capsular bag 14 and an external or contact lens 93 comprising at least in part of light polarizing material. The assembly polarizes at least part of the central light and/or at least part of peripheral light. In this non-limiting example the peripheral part 97 of retina 19 is dark due to the relative angle between lenses 1 and 93 and the central part is illuminated and not polarized. Intra ocular implant 1 has a central area 95 with different polarizing angle than the peripheral area 96. External implant 93 is shown in this example to have the same polarizing effect on its whole surface but the current configuration also includes a possibility of different polarizing angles on external lens 93 as well. The external lens 93 is possibly adjustable by the patient so as to control the amount of light reaching the retina on any part of the retina and it can be replaced by another external lens for the same purpose.

Finally, reference is made to FIG. 18, illustrating a non-limiting example of an intra ocular implant for improving the vision of a patient in which future development of retinal disorders may occur. In this example the optical arrangement includes two mirrors 3 and 4 located beneath the iris 13 out of the visual axis. Intra ocular lens 1 has been implanted in a prior cataract surgery in a patient who does not suffer from any retinal disease. Since the mirrors 3 and 4 are beneath the iris 13, they are unfelt by the patient who sees light 16 reaching the retina and creating image 72, which is unmagnified. The optical arrangement may comprise of at least one additional lens 40, in this example an external lens to the eye, (but could also be a contact lens or a second intra ocular lens). The additional lens comprises element 33 (being a diffractive optics element, liquid crystal elements, Fresnel prism or other prism), which may be located in the interior, anterior surface, posterior surface or mechanically attached to lens 40 and may cover any part or the whole of the lens surface. If the patient develops a retinal disease that can be assisted by central magnification, element 33 diverts light 26 to mirrors 3 and 4 creating a magnified image on the retina. At least one additional unmagnified image may be also be created on the retina 19.

The invention claimed is:

1. An intra ocular implant for magnifying an incoming image comprising:
   an optical axis;
   a body member having optical properties; and,
   an optical arrangement having a second axis perpendicular to said optical axis, said optical arrangement adapted to form, on a retina of a patient with a diseased central retina, at least one magnified image relative to the incoming image,
   wherein the magnified image comprises at least part of a peripheral visual field and at least part of a central visual field,
   said optical arrangement comprising said body member and only at least two mirrors, said at least two mirrors not extending to a radially outermost edge of said body member along said second axis;
   wherein said mirrors are adapted to reflect natural visible, ambient light onto the retina in a light path comprising said at least part of the peripheral visual field and said at least part of the central visual field, said mirrors comprising a reflective coating wherein the reflective coating is a dielectric coating having multiple thin layers applied in a vaporized form; and at least part of said implant is further coated with at least one protective biocompatible coating layer.

2. The implant according to claim 1, wherein at least one selected from a group consisting of said body member, said optical arrangement, a means of fixation into an eye or any combination thereof is interchangeable after surgery.

3. The implant according to claim 1, wherein at least part of said body member is adapted to be located under the iris.

4. The intra ocular implant according to claim 1, being adapted to create perceivable differences between said at least part of the peripheral visual field on the retina and said at least part of the central visual field on the retina, hence enabling the patient to differentiate between said visual fields;
wherein said perceivable differences are based on one or more criteria selected from a group consisting of differences in contrast, location, transmitted light spectra, color, magnification, illumination or focus.

5. The intra ocular implant according to claim 1, wherein said implant is adapted to be implanted in a pseudophakic eye.

6. The implant according to claim 1, wherein said at least two mirrors are mechanically attached to or vaporized on anterior and/or posterior surfaces of said implant; wherein said anterior and/or posterior surfaces are characterized by any predetermined shape selected from the group consisting of a niche, hole, depression and a combination thereof.

7. The intra ocular implant according to claim 1 wherein said implant comprises an anterior and/or posterior surface, said anterior and/or posterior surface having a shape chosen from the group consisting of aspheric, multifocal, fisheye, irregular, and a shape that corrects higher order optical aberrations.

8. An intra ocular implant for implantation in the interior of a human eye for magnifying an incoming image, the eye having a pupil opening diameter, the implant comprising:
a body member having optical properties, wherein said body member has a diameter configured to be greater than the pupil opening diameter; and,
an optical arrangement adapted to form, on a retina of a patient with a diseased central retina, at least one magnified image relative to the incoming image,
wherein the magnified image comprises at least part of a peripheral visual field and at least part of a central visual field,
said arrangement comprising said body member and at least one optical element selected from the group consisting of diffractive optics elements, adaptive optics elements, Fresnel prisms, lenses, liquid crystal elements, mirrors, prisms and any combination thereof;
wherein said implant comprises at least one mirror adapted to reflect natural visible, ambient light onto the retina in a light path comprising said at least part of the peripheral visual field and said at least part of the central visual field, said mirror comprising a reflective coating wherein the reflective coating is a dielectric coating having multiple thin layers applied in a vaporized form; and
at least part of said implant is further coated with at least one protective biocompatible conformal polymer coating layer comprising a polyxylylxene polymer.

9. The implant according to claim 8, adapted to be fixed to a pseudophakic eye by a method selected from the group consisting of anterior chamber fixation, posterior chamber fixation, capsular bag fixation, scleral fixation, intra-vitreous fixation, sulcus fixation, and iris supported fixation.

10. The implant according to claim 8, wherein said at least one mirror is mechanically attached to or vaporized on anterior and/or posterior surfaces of said implant; wherein said anterior and/or posterior surface is characterized by any predetermined shape selected from the group consisting of niche, hole, depression and a combination thereof.

11. The implant according to claim 8, wherein at least one element selected from the group consisting of said body member, said optical arrangement, a means of fixation into the eye or any combination thereof is interchangeable after surgery.

12. The intra ocular implant according to claim 8, wherein said optical element has a shape chosen from the group consisting of aspheric, multifocal, fisheye, irregular, and a shape that corrects higher order optical aberrations.

13. An intra ocular implant (IOL) for implantation in the interior of a human eye anterior to a pre-existing IOL, the eye having a pupil opening diameter, the implant comprising:
a body member having optical properties, wherein said body member has a diameter configured to be greater than the pupil opening diameter, and
an optical arrangement adapted to form, on a retina of a patient with a diseased central retina, at least one magnified image relative to an incoming image,
wherein the magnified image comprises at least part of the peripheral visual field and at least part of the central visual field,
said arrangement comprising said body member and at least one optical element selected from the group consisting of diffractive optics elements, adaptive optics elements, Fresnel prisms, lenses, liquid crystal elements, mirrors, prisms and any combination thereof,
wherein said implant comprises at least one mirror adapted to reflect natural visible, ambient light onto the retina in a light path comprising said at least part of the peripheral visual field and said at least part of the central visual field, said at least one mirror comprising a reflective coating wherein the reflective coating is a dielectric coating having multiple thin layers applied in a vaporized form,
and wherein said implant has no dioptric power and is adapted to be fixed to a pseudophakic eye by a method selected from the group consisting of anterior chamber fixation, posterior chamber fixation, capsular bag fixation, scleral fixation, intra-vitreous fixation, sulcus fixation, and iris supported fixation.

14. The intra ocular implant according to claim 13, wherein said implant comprises an anterior and/or posterior surface, said anterior and/or posterior surface having a shape chosen from the group consisting of aspheric, multifocal, fisheye, irregular, and a shape that corrects higher order optical aberrations.

15. An intra ocular implant for magnifying an incoming image comprising:
an optical axis;
a body member having optical properties; and,
an optical arrangement having a second axis perpendicular to said optical axis, said optical arrangement adapted to form, on a retina of a patient with a diseased central retina, at least one magnified image relative to the incoming image,
wherein the magnified image comprises at least part of the peripheral visual field and at least part of the central visual field, said optical arrangement comprising said body member and only at least two mirrors, said at least two mirrors not extending to a radially outermost edge of said body member along said second axis;

wherein said mirrors are adapted to reflect natural visible, ambient light onto the retina in a light path comprising said at least part of the peripheral visual field and said at least part of the central visual field.

\* \* \* \* \*